(12) United States Patent
Menachem et al.

(10) Patent No.: US 9,097,685 B2
(45) Date of Patent: Aug. 4, 2015

(54) ADVANCED INSPECTION METHOD UTILIZING SHORT PULSES LED ILLUMINATION

(71) Applicants: Amnon Menachem, Zefat (IL); Yossi Cherbis, Haifa (IL); Arnon Ben Natan, Kiriat Tivon (IL)

(72) Inventors: Amnon Menachem, Zefat (IL); Yossi Cherbis, Haifa (IL); Arnon Ben Natan, Kiriat Tivon (IL)

(73) Assignee: CAMTEK LTD., Migdal Haemek (IL)

( * ) Notice: Subject to any disclaimer, the term of this patent is extended or adjusted under 35 U.S.C. 154(b) by 54 days.

(21) Appl. No.: 13/975,384

(22) Filed: Aug. 26, 2013

(65) Prior Publication Data
US 2014/0055781 A1    Feb. 27, 2014

Related U.S. Application Data

(63) Continuation of application No. 13/110,015, filed on May 18, 2011, now Pat. No. 8,520,200.

(60) Provisional application No. 61/347,477, filed on May 24, 2010.

(51) Int. Cl.
| | |
|---|---|
| *G01N 21/00* | (2006.01) |
| *G01N 21/95* | (2006.01) |
| *G01N 21/956* | (2006.01) |
| *G01N 21/94* | (2006.01) |

(52) U.S. Cl.
CPC ............ *G01N 21/9501* (2013.01); *G01N 21/94* (2013.01); *G01N 21/956* (2013.01)

(58) Field of Classification Search
CPC .. G01N 21/9501; G02B 21/16; G02B 27/145; G02B 27/149; G02B 26/008; G02B 27/0994; G02B 27/1006; G02B 27/102; G02B 27/1033; G02B 19/0028; G02B 19/0066; G02B 21/0076; G02B 21/008; G02B 21/361; G02B 6/0036
USPC ............................................ 356/237.1–237.5
See application file for complete search history.

(56) References Cited

U.S. PATENT DOCUMENTS

| | | | |
|---|---|---|---|
| 2004/0041702 A1 | 3/2004 | Toulmin et al. | |
| 2007/0206183 A1* | 9/2007 | Lebens | ...................... 356/237.2 |
| 2009/0257050 A1 | 10/2009 | Pertzov et al. | |

* cited by examiner

*Primary Examiner* — Michael P Stafira
(74) *Attorney, Agent, or Firm* — Oren Reches

(57) ABSTRACT

An illumination module that may include a LED driver; a group of light emitting diodes (LEDs) that comprises at least one LED; the group of LED is coupled to the LED driver; wherein the LED driver is arranged to activate the group of LEDs by driving a high current short duration driving signal; and wherein the group of LEDs is arranged to emit at least one light pulse in response to the high current short duration driving signal.

21 Claims, 24 Drawing Sheets

260

ADVANCED INSPECTION METHOD UTILIZING SHORT PULSES LED ILLUMINATION

RELATED APPLICATIONS

This application is a continuation application of U.S. patent application Ser. No. 13/110,015 filed 18 May 2011 that claims priority from U.S. provisional patent filing date May 24 2010 Ser. No. 61/347,477, both being incorporated herein by reference.

BACKGROUND

Advanced inspection systems may use either one of two illumination methods: continuous illumination and strobe illumination. In continuous illumination the object and the camera move continuously one with respect to the other while the object is illuminated continuously.

Linear sensors such as CCD linear array or CCD-TDI are used to acquire the image. In the strobe illumination method the object and the camera also move continuously one with respect to the other, but the object is illuminated with short pulses of light. The strobe illumination method enables the use of 2D sensors such as 2D CDD arrays or MOS arrays. The pulse duration of the light source and the scanning speed are adjusted such that the movement of the image with respect to the camera during the light pulse will be at the order of one pixel or less. Common pulsed illumination sources are pulsed lasers and gas discharge flash lamps (i.e. Xe discharge lamp).

Light sources such as discharge lamps, and especially Xe lamps are characterized by long fall time or "tail" as illustrated in FIG. 1 which can go up to 10 µS or more.

Discharge lamps tail also imposes severe limitation on the maximal possible pulse rate (or frame rate) as will be clear from the following example. When using a 1000×1000 pixels camera operating at 500 frames per second, with a single pulse of light per frame—during the frame time (2 mS), the camera and the article move approximately 1000 pixels one with respect to the other to enable acquisition of next frame. In order to ensure image smear of less than 1 pixel during the light pulse, the pulse duration should be less than 2 µS, which is significantly less than what discharge lamps can provide.

SUMMARY OF THE INVENTION

According to an embodiment of the invention an inspection system may be provided and can include an illumination module that may include a LED driver; a group of light emitting diodes (LEDs) that may include at least one LED; the group of LED may be coupled to the LED driver; wherein the LED driver may be arranged to activate the group of LEDs by driving a high current short duration driving signal; and wherein the group of LEDs may be arranged to emit at least one light pulse in response to the high current short duration driving signal.

The high current short duration driving signal has a current that exceeds 100 Amperes.

The current short duration driving signal has a current that exceeds a maximal allowable current to be provided to the group of LEDs when operating in a continuous illumination mode.

The illumination module may include multiple groups of LEDs.

The illumination module may include multiple groups of LEDs, each group of LEDs being controlled independently from other groups of LEDs.

The group of LEDs may be arranged in a ring formation and wherein each LED is followed by optics for directing light from the LED towards an article.

The illumination module may include multiple groups of LEDs that are arranged in a concentric rings formation and wherein each LED may be followed by optics for directing light from the LED towards an article.

The group of LEDs may include multiple sets of LEDs; the spectrum of light pulses of different LEDs of each set of LEDs differs from each other; the light pulses from LEDs of the same set of LEDs are directed towards a single light guide; each light guide may be arrange to output light pulses that have a spectrum that may be a superposition of the spectrums of light pulses from the LEDs of the set of LEDs.

The illumination module may include multiple groups of LEDs and multiple hollow concentrators that are located in a first plane; wherein each hollow concentrator may be positioned to receive lights pulses from a group of LEDs, and direct the light from the group of LEDs towards an article that may be positioned outside the first plane.

The groups of LEDs are positioned at an annular formation; wherein the multiple hollow concentrators have a parabolic shape and radially extend from a center of the illumination module.

The illumination module may include multiple groups of LEDs that are positioned in a half dome formation.

The illumination module may include a collimator, a filter, a homogenizer and a concentrator; wherein the group of LEDs may be arranged to illuminate the collimator by light pulses; wherein the collimator collimates the light pulses to provide collimated light pulses; wherein the filter may be arranged to spectrally filter the collimated light pulses to provide filtered light pulses; wherein the homogenizer may be arranged to increase an illumination homogeneity of the filtered light pulses to provide homogenized light pulses; wherein the concentrator may be arranged to concentrate the homogenized light pulses onto a light guide.

The concentrator may be a compound parabolic concentrator; and wherein the filter belongs to a set of replaceable filters.

The illumination module may include a LED base element that may be coupled to at least a portion of the group of LEDs; at least one connector arranged to be connected to the LED base element; an annular base the may be coupled to the at least one connector; the at least one connector and the annular base are made of heat conducting material for dissipating heat generated by the at least portion of the LEDs.

The illumination module may include multiple LED base elements; multiple connectors and multiple annular bases; a plurality of LEDs is connected to each LED base element; different LED base elements are connected to multiple concentric annular bases.

The multiple annular bases are positioned at different heights and wherein at least one segment of a lens array may be connected to each annular base.

The multiple annular bases are positioned at different heights and multiple segments of lens arrays are connected to a single annular base.

The illumination module may include multiple segments of lens arrays that are forced against each other, once assembles, by spring elements.

The illumination module may include multiple lens array segments, wherein lens array segments differ from each other by at least one of a height of assembly and angular range.

The inspection system may also include a sensor for generating detection signals in response to light from an inspected object; the inspected object may be a semiconductor wafer or a printer circuit board; and a processor for processing the detection signals.

The system may include multiple groups of LEDs.

The system may include multiple groups of LEDs, each group of LEDs being controlled independently from other groups of LEDs.

The group of LEDs may be arranged in a ring formation and wherein each LED may be followed by optics for directing light from the LED towards an article.

The system may include multiple groups of LEDs that are arranged in a concentric rings formation and wherein each LED may be followed by optics for directing light from the LED towards an article.

The group of LEDs may include multiple sets of LEDs; the spectrum of light pulses of different LEDs of each set of LEDs differs from each other; light pulses from LEDs of the same set of LEDs are directed towards a single light guide; each light guide may be arrange to output light pulses that have a spectrum that may be a superposition of the spectrums of light pulses from the LEDs of the set of LEDs.

The system may include multiple groups of LEDs and multiple hollow concentrators that are located in a first plane; each hollow concentrator may be positioned to receive light pulses from a group of LEDs, and direct the light from the group of LEDs towards an article that may be positioned outside the first plane.

The groups of LEDs are positioned at an annular formation; wherein the multiple hollow concentrators have a parabolic shape and radially extend from a center of the illumination module.

The multiple groups of LEDs are positioned in a half dome formation.

The system may include a collimator, a filter, a homogenizer and a concentrator; wherein the group of LEDs may be arranged to illuminate the collimator by light pulses; the collimator collimates the light pulses to provide collimated light pulses; the filter may be arranged to spectrally filter the collimated light pulses to provide filtered light pulses; the homogenizer may be arranged to increase an illumination homogeneity of the filtered light pulses to provide homogenized light pulses; the concentrator may be arranged to concentrate the homogenized light pulses onto a light guide.

The concentrator may be a compound parabolic concentrator; and wherein the filter belongs to a set of replaceable filter.

A method for inspecting an article may be provided and may include: generating, by a light emitting diode (LED) driver, a high current short duration driving signal; transmitting the high current short duration driving signal to a group of LEDs; emitting at least one light pulse by the group of LEDs in response to the high current short duration driving signal; and illuminating the article by the light pulse.

The method may include generating light pulses by multiple groups of LEDs.

The method may include independently controlling each group of LEDs out of multiple groups of LEDs.

The group of LEDs may be arranged in a ring formation and wherein each LED may be followed by optics for directing light from the LED towards an article.

The method may include emitting multiple light pulses by multiple groups of LEDs, the multiple groups of LEDs that are arranged in a concentric rings formation and wherein each LED may be followed by optics for directing light from the LED towards an article.

The group of LEDs may include multiple sets of LEDs; the spectrum of light pulses of different LEDs of each set of LEDs differs from each other; wherein the method may include: directing light pulses from LEDs of the same set of LEDs towards a single light guide; and outputting, by each light guide, light pulses that have a spectrum that may be a superposition of the spectrums of light pulses from the LEDs of the set of LEDs.

The method may include: emitting multiple light pulses by multiple groups of LEDs towards multiple hollow concentrators that are located in a first plane; receiving, by each hollow concentrator, the multiple lights pulses; and directing, by each hollow concentrator, a light pulse from the group of LEDs towards an article that may be positioned outside the first plane.

The groups of LEDs are positioned at an annular formation; wherein the multiple hollow concentrators have a parabolic shape and radially extend from a center of the illumination module.

The method may include emitting multiple light pulses by multiple groups of LEDs that are positioned in a half dome formation.

The method may include illuminating, by the group of LEDs, a collimator with light pulses; collimating the multiple light pulses by the collimator to provide collimated light pulses; spectrally filtering, by a spatial filter, the collimated light pulses to provide filtered light pulses; increasing, by a homogenizer, an illumination homogeneity of the filtered light pulses to provide homogenized light pulses; and concentrating, by a concentrator, the homogenized light pulses onto a light guide.

The concentrator may be a compound parabolic concentrator; and wherein the filter belongs to a set of replaceable filter.

The method may also include illuminating the article by the light pulses; generating, by a sensor, detection signals in response to light from an inspected object; the inspected object may be a semiconductor wafer or a printer circuit board; and processing the detection signals.

The method may include transmitting the high current short duration driving signal via a LED base element to a group of LEDs; the LED base element may be coupled to at least a portion of the group of LEDs; the LED based element may be connected to at least one connector; the at least one connector may be coupled to an annular base; wherein the at least one connector and the annular base are made of heat conducting material; and dissipating heat generated by the at least portion of the LEDs by the at least one connector and the annular base.

The method may include emitting multiple light pulses by multiple groups of LEDs in response to the high current short duration driving signals; wherein the multiple groups of LEDs are coupled to multiple LED base elements, multiple connectors and multiple annular bases; wherein different LED base elements are connected to multiple concentric annular bases.

The multiple annular bases are positioned at different heights and may include at least one segment of a lens array may be connected to each annular base.

The multiple annular bases are positioned at different heights and multiple segments of lens arrays are connected to a single annular base.

The method may include directing the multiple light pulses via multiple lens array segments, wherein the multiple lens array segments are forced against each other, once assembles, by spring elements.

The method may include directing the multiple light pulses via multiple lens array segments, wherein the lens array segments differ from each other by at least one of a height of assembly and angular range.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

Figure 1:
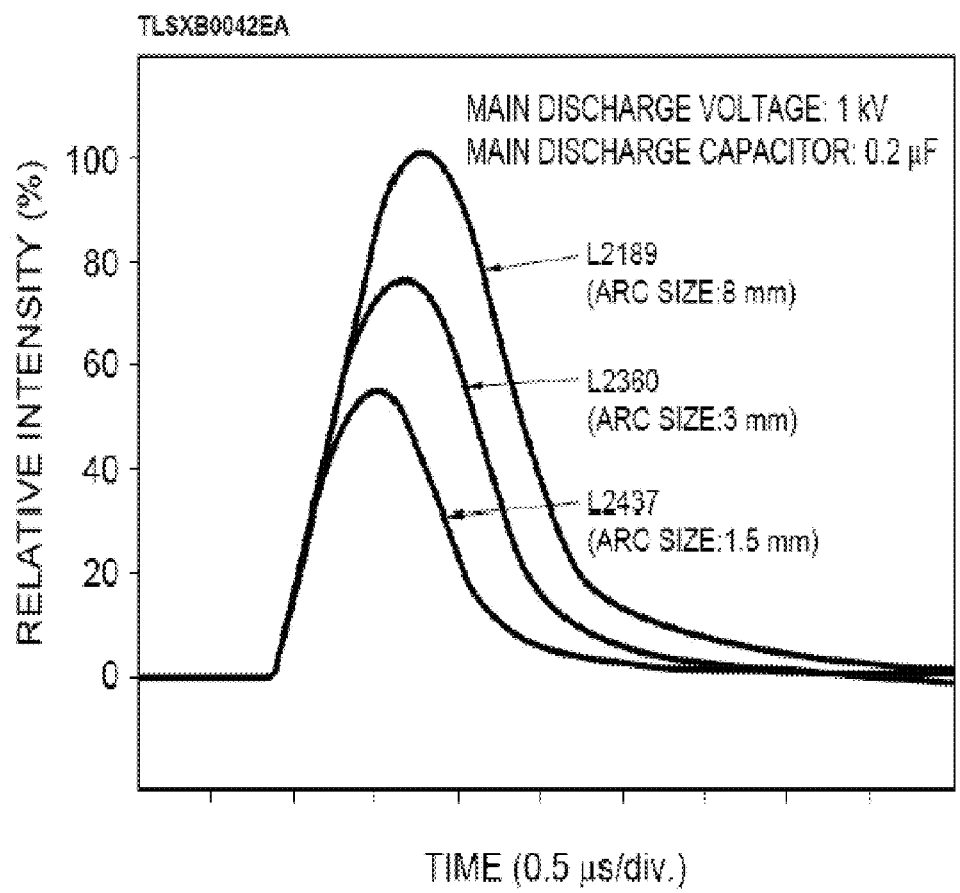
FIG. 1 illustrates a timing diagram of a prior art discharge lamp.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In all figures the same reference numbers represent the same elements.

Throughout this specification "light emitting diode" (LED) also includes Laser Diodes (LDs). A LED may be a semiconductor light source and a LD is a laser that may include a semiconductor active medium.

There are provided inspection systems and methods using LEDs for strobe illumination either at low or very high pulse currents in the order of 100 A and above, much beyond the specified maximum current dictated by LED manufacturers.

A system is provided that utilizes light emitting diodes (LED) that are fed by high current and may provide short light pulses of adequate intensity.

The term high current can include current that may exceed 30 Amperes, 40 Amperes, 50 Amperes, 60 Amperes, 70 Amperes, 80 Amperes, 90 Amperes, 100 Amperes, 110 Amperes, 120 Amperes, 130 Amperes, 140 Amperes, 150 Amperes, 160 Amperes, 170 Amperes, 180 Amperes, 190 Amperes, 200 Amperes, 210 Amperes, 220 Amperes, 230 Amperes, 240 Amperes, 250 Amperes, 260 Amperes, 270 Amperes, 280 Amperes, 290 Amperes, 300 Amperes and more.

A high current can be a current that exceeds the maximum allowable current that can be supplied to a LED when operating in a continuous illumination mode.

The system can include LED drivers that provide the high current to the LEDs using a strip cable that includes multiple conductors that have a large form factor and are made of copper or other material that has high conductivity and low inductance. For example, conductor having a cross section of about 1.26 centimeter by 25-150 microns can be used. The distance between adjacent conductors can be 25 to 150 microns. The gap between adjacent conductors can be filled with a material such as Kapton that has a very high dielectric coefficient.

Using such a strip cable can reduce (and even minimize) distortions introduced in pulse current and may illustrate low current losses.

According to various embodiments of the invention multiple LEDs and optionally associated optics can be positioned in a symmetrical manner about an axis, wherein each group of one or more LED can be controlled independently from other groups of LEDs.

The advent of high power LEDs (Light Emitting Diodes) provides for many advantages over the use of discharge flash lamps.

Among these advantages:
a. LED provide for higher scanning speeds:
   i. LED sources pulse duration is practically limited only by the driving electronics. Specifically, LED fall time follows the driving current immediately, and therefore falls down to zero within typically only a few tens of nS. On the other hand LED rise time depends on the LED die area, LED die structure design and LED packaging. The typical rise time of a large die may go down to 200 nS or even below this value at high pulse current drive. Therefore pulse durations as short as 250 ns are possible. As a result LED illumination provides for higher scanning speeds.
b. LEDs provide for easy control of pulse duration ranging from down to few hundreds of nanosecond and up to continuous illumination where the only limitation is the allowable current at the given data cycle. This enables flexibility in selection of short pulses with high illumination intensity for fast scanning modes or longer pulses with reduced illumination intensity for reduced scanning speed.
c. LEDs also provide for better control of light pulse shape.
d. LEDs are smaller in size and therefore provide for more compact design. The small inherent size of LEDs also enables:
   i. Use multiple LED chips on a single package and other compact packaging for:
      a. Increased illumination intensity
      b. Increased illumination uniformity
      c. Flexibility in spatial and angular design of illumination (i.e flexibility in design of special dark field illumination configurations)
      d. Versatile options of controlling different light spectrum or a mixed spectrum of various LED chips.
   ii. Flexible integration of additional optical components for more optimal and efficient illumination (i.e. light guides, micro-lenses, fibers and like). See dark field illumination configuration options.
e. Discharge lamps illumination has broad spectral range, with significant radiation at the UV and IR region. As a result, a significant amount of heat needs to be removed, which further complicates discharge lamps packaging. LEDs provide narrower spectrum with substantially no UV and IR radiation and therefore heat dissipation is limited.
f. Unlike discharge lamps where there is a need of a special color filter in order to choose a certain spectral range, LEDs are available in a wide variety of colors—white, green, red, blue and packages, which include RGB or RGBY LEDs on the same substrate. This enables enhanced features of spectral dependence inspection. See an example of such use under dark field illumination configuration options.

g. LEDs typically have much longer life time even at currents as high as 100 A and above.

h. LEDs pulse to pulse variations of intensity and uniformity is better.

The description below will refer to an inspection system operating with strobe illumination, and specifically, to the use of LEDs as the pulsed light source and at exceptional high pulse current operation.

Figure 2:
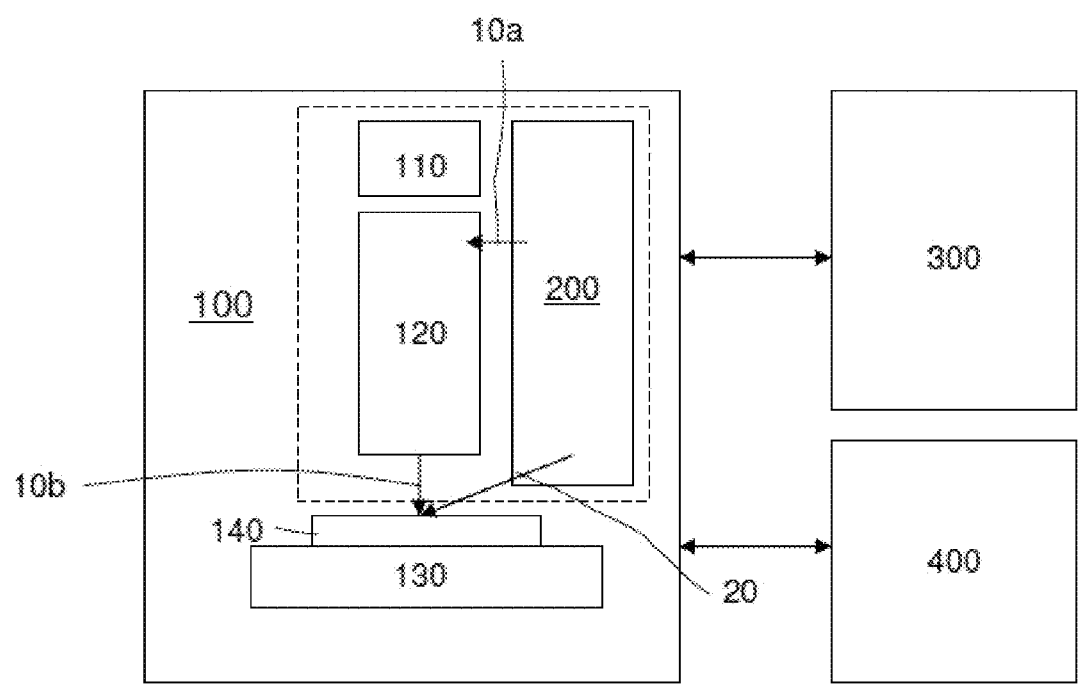
FIG. 2 illustrates a system according to an embodiment of the invention.

FIG. 2 depicts a block diagram of system 100 according to an embodiment of the invention. The system 100 can be an automatic optical inspection (AOI) system.

An article 140 is placed on a stage 130 and can be moved within an XY plane. The article 140 may be a semiconductor wafer, a printed circuit board and alike.

Illumination module 200 illuminates the article in one or more manners:

a. Bright field illumination—the illumination module 200 illuminates the article 140 through part of the imaging optics 120. The illumination module 200 sends ray 10a to the imaging optics 120 that in turn directs ray 10b towards the article 140. The illumination and collection zones (for example—cones) are identical.

b. Dark field illumination—the illumination module 200 illuminates the article 140 by ray 20 that is located outside the collection zone of the imaging optics 120. Light from the article 140 is diffused (or scattered) or partially diffused by virtue of the interaction of illuminated light and the article substance.

In either case part of the scattered and, additionally or alternatively, reflected light form the article 140 may be acquired by camera 110 and further processed by image computer 300. The overall operation of the system 100 may be controlled by system controller 400.

Figure 3:
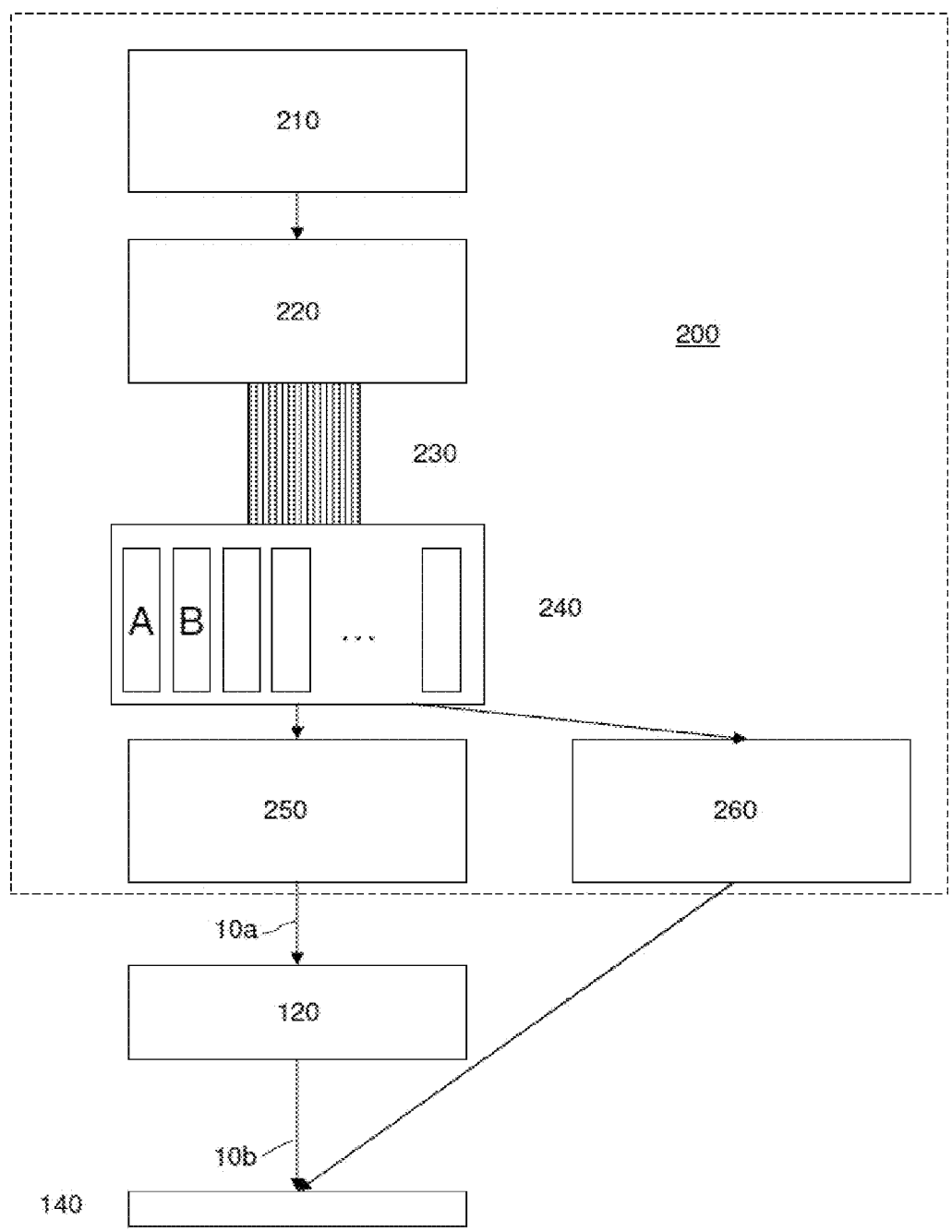
FIGS. 3-18 illustrate various portions of the system according to various embodiment of the invention.

Details of the illumination module are now explained with reference to FIG. 3 Controller 210 controls all the required parameters of the light pulses: pulse timing, pulse durations, pulse shape, pulse currents, data cycle, starts and ends of pulse streams, etc.

The controller 210 also may be configured to control multiple data streams (multiple control signals or control sequences to the LED drivers) at the same time, where each data stream may have its own operational parameters—so that each group of one or more LEDs can be controlled independently.

Control data from the data controller 210 may be transferred to one or more LED drivers such as one or more high current pulse current generators 220. FIG. 3 illustrates multiple LED drivers.

The LED drivers 220 output high current signals, (in response to the data streams from the controller 210) that are sent to illumination units (denoted A, B . . . K) of the light sources module 240. Each illumination unit may include a group of one or more LEDs and may optionally include optics.

Each illumination unit can be fed by a single channel such as one or more strip cables (or strips). It is noted that multiple illumination units can be fed by the same strip cable or otherwise receive the same high current short duration pulses.

Using several strip cables provide higher throughput and may allow to simultaneously transfer multiple data streams of high data rate, short pulses of high-currents, to a relatively long distance with minimal pulse distortions or losses of pulse energy. This configuration enables the following operating parameters:

a. Rise time may be mainly dictated by the light source response time. For large die LEDs and at high pulse current of 100 A (as an example) it may be typically few hundreds of nano-Seconds. Typical response time value of the system under pure proper resistance load may be <100 nS.

b. Pulse currents of 200-300 A or even higher.

All the above parameters may be achievable with strip cable. The length of the cable may be not an issue if properly designed. A 1.5-2 meter length was practically approved to work very well in such system.

Typical operating conditions will use 100 to 160 A current at 140 Hz and various pulse durations ranging from 0.5 to 4 μS (or higher depending on LED type and pulse current).

These currents are approximately twenty times larger than the maximal current usually allowed by LEDs manufacturers for continuous operation of the LEDs.

As a result light intensity and the amount of light energy contained within the pulse increases accordingly though not linearly at the high end zone of the current scale.

Any of the illumination units A, B, etc. within light sources module 240 may represent a group of one or more diodes. A group of diodes can include diodes of different types. For example a group of diodes can include one or more LED and one or more LD. A group of LEDs can include an array of LEDs. For simplicity of explanation the group of diodes is referred to as g a group of LEDs.

It is noted that each illumination unit may also include miniature optics such as lenses.

Each of the illumination units (A, B, etc.) can receive different inputs originating from different channels of the pulse generator 220 and strip cable 230, and therefore may operate with different parameters (i.e. different current, pulse shape/width, pulse timing and like).

Each illumination unit can transmit light that may be directed towards the article via the bright field module 250 and imaging optics 120 to provide bright field illumination. Additionally or alternatively, the light from each illumination unit can be sent to dark field module 260 to provide dark field illumination.

It is noted that the light of one or more illumination units can be directed to the bright field module 250 while light from one or more other illumination unit can be directed to the dark field module 260.

Light emitted from either imaging optics 120 or dark field module 260 may illuminate article 140.

Transferring high current high frequency short duration driving signals through standard electrical conductive wire (circular in cross section, twisted pair, etc) is prone to severe loss of signal integrity. This loss may be manifested in many forms such as by loss of the original pulse shape (as originated at the signal generator output), the signal rise time is slowed, the signal intensity is reduced, etc, as the data signal wave is propagating through the conductive wire.

The characteristic impedance of a uniform transmission line is defined by:

$$Z_0 \propto \sqrt[2]{\frac{L}{C}}.$$

In order to achieve very low impedance one should thus increase the capacitance and decrease the inductance. When a high current high frequency short duration driving signal is transmitted through a conductive wire a significant magnetic flux fields may be created around the cable, which may oppose signal current changes through the conductive wire. By setting the two conductive wires of a transmission line wide enough along with very small gap filled with a good dielectric material in between them, the capacitance is decreases and the magnetic field is weakens contributing to unwanted current cancelation and low inductance. Another important figure of a transmission line is its impedance matching to the load (e.g. LED) it is driving Impedance matching is considered good when transmission line $Z_o$ is equals to the load impedance. Optimum energy transfer with minimum reflections back to the driving source is achieved when the transmission line is having characteristic impedance which is matching the load impedance. Thus using a proper strip cable consists of two wide conducting wires of few tens mm width with a thin gap of few tens of microns separating between these wires which is filled by a proper dielectric material should assist in solving these apparent problems and serve as a good transmission line for high frequency current signals.

According to an embodiment of invention a strip cable included in the system is manufactured by LIC Engineering 3735 Coffey Lane Santa Rosa, Calif. 95403 USA.

Thus, using a strip cable to high current short duration driving signal may be unique in order to preserve the shape of the high current short duration driving signal along the transmission line and thus utilize the optimum light energy (contained within the pulse light signal) from the light source device that is being driven.

According to an embodiment of the invention there may be an option to introduce a delay between high current short duration driving signals sent to different groups of LEDs. The delay enables reducing the high output voltage requirement of the current generator due to high forward voltage drop which may be the sum of the forward voltage drop of each LED in the groups of LEDs. A delay may be introduced between LEDs of the same group of LEDs. Such a delay has the advantage of toggling in between different LED groups during a single article scan.

Figure 4:
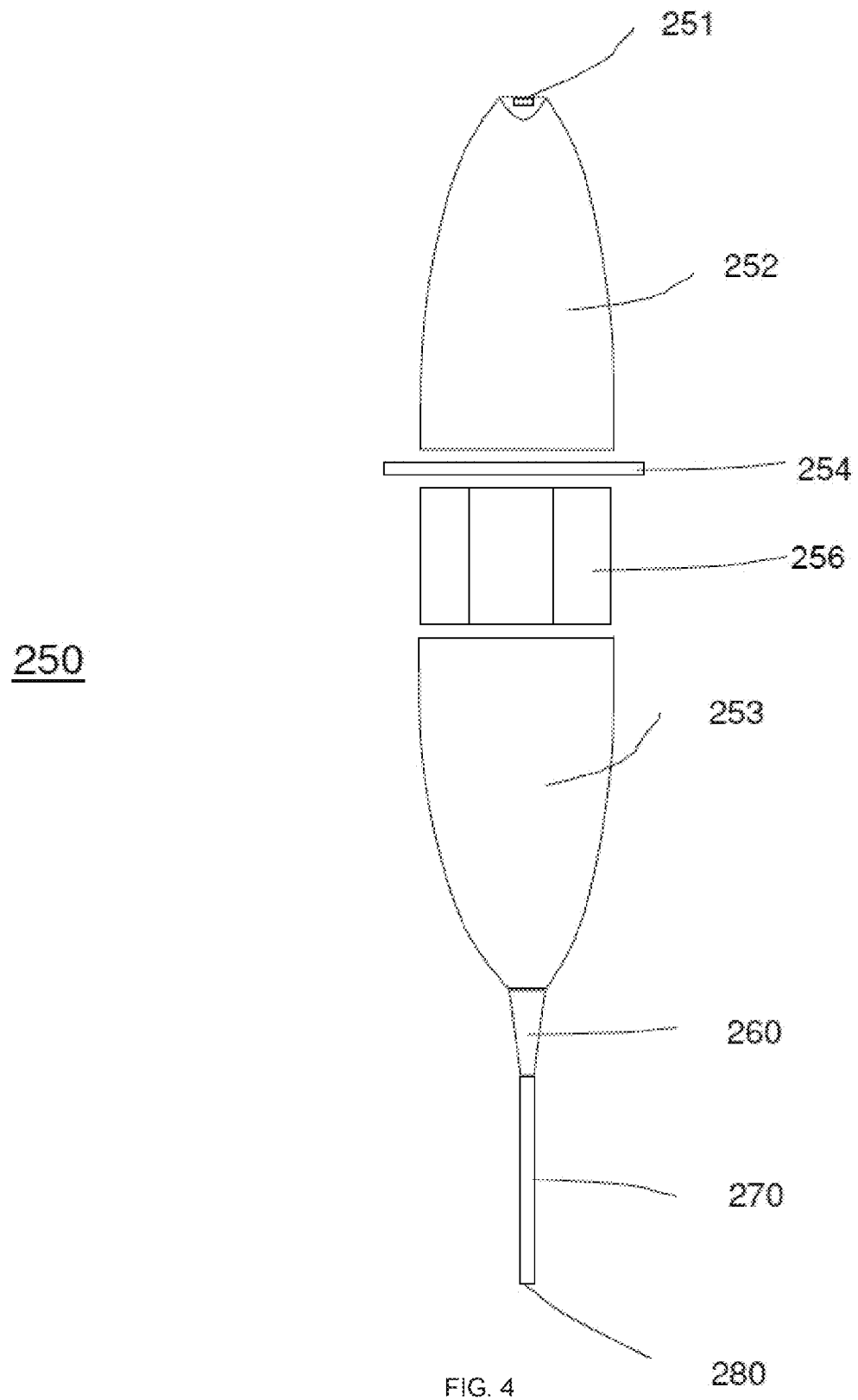

Details of the bright field module 250 are now explained with reference to FIG. 4.

An illumination unit 251 may be located on top of a collimator 252 such as to illuminate the collimator.

The illumination unit 251 may be followed (or include) miniature lenses.

Collimator 252 may be configured to collect maximal amount of light from all LED area and its angular divergence and convert it to a quasi-collimated illumination at the output of the collimator.

The collimator in this example is a non-imaging CPC (Compound Parabolic Concentrator) type or any modification of that, which may be made of a high index of refraction material, for example Acrylic material or any other high index of refraction material either hollowed with mirror faces device or a solid bulky material device with mirror faces coating outside the device. Modification to such CPC could be any likewise Total Internal Reflection (TIR) based design with or without a lens curved top at the device output aperture.

The quasi collimated light may be then transferred through a selectable filter module 254 which may consist of spectral filters, OD filters, polarizing filters, and any combinations of the above.

The light may be then transferred through a homogenizer 256, which may be type of kaleidoscope (or other homogenizer) of the hexagonal shape (or other shape such as square, triangle, etc.) in cross section. The homogenizer may be configured to produce a more homogeneous illumination—spatially as well as angularly—at its output.

The light may be then transferred to a concentrator 253, having a structure similar to collimator 252, but not necessarily with the same optical parameters. The concentrator, together with or without the tapered waveguide 260, adapts the illumination to conform to the optical parameters of the imaging optics 120, such as the needed illumination area (size and shape) and angular content (which, for Koehler illumination as in this example, determines the illuminated FOV). The light may then be transferred directly or via optical fiber 280 to the imaging optic 120. The end surface 280 of fiber 270 or the end surface of 260 may be finally applied instead of 504 in FIG. 5.

Figure 5:
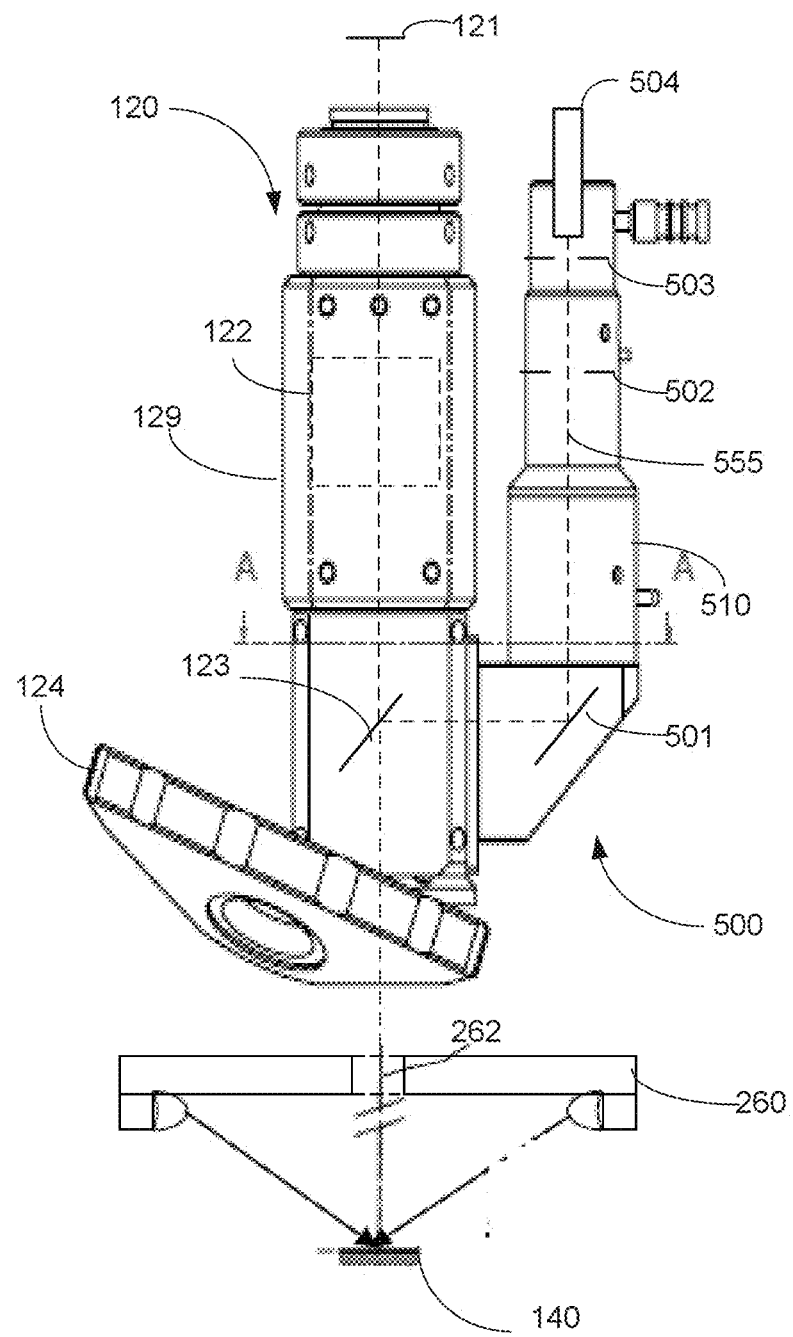
Figure 6:
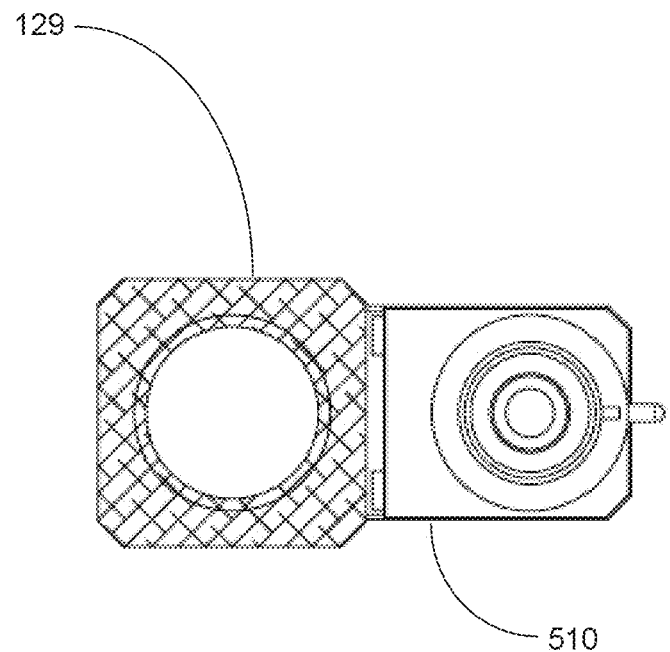

FIGS. 5 and 6 illustrate a bright field path 500 that does not use LEDs and a dark field path 260 that includes LEDs that are powered by high currents according to an embodiment of the invention. These figures also illustrate an imaging optics 120 that images the illuminated area over the article 140 onto imaginary plane 121.

FIG. 5 illustrates various optical components (122, 123, 124, 501, 502, 503, and 504) and mechanical elements 129 and 500 that provide support to the optical elements. FIG. 6 is a cross sectional view of the mechanical elements 129 and 500 along a horizontal plane denoted AA.

The imaging optics 120 includes an imaging lens 122, a beam splitter 123 and a turret 124 of objective lenses. The turret includes multiple objective lenses (that differ from each other) and by rotational movement of the turret 124—the selected objective lens is positioned at the path of reflected or scattered light from the article 140.

Light from the article 140 passes through an aperture 262 (that may be positioned at the center of symmetry of the dark field illumination unit 260 and especially at a center of supporting element 269), passes through a selected objective lens of turret 124, passes through beam splitter 123 and passes through the imaging lens 122.

The bright field path 500 starts by a light guide 504 that provides light from a light source, light passes through an aperture diaphragm 503, passes through field stop 502 and may be deflected by mirror 501 towards beam splitter 123. The beam splitter 123 directs the light through aperture 262 towards the article 140.

Typical parameters of the illumination at the end surface 280 are clear aperture of 6.5 mm and NA of 0.66.

It is noted that different designs may lead to modifications of this embodiment, such as the elimination of the homogenizer, tapered waveguide and optical fiber, or even, for example, elimination of a filter and homogenizer altogether to form one solid optical element which includes the collimator and concentrator. Other designs may include a lens instead of the collimator to collect the light from light source and collimate it on to the filter or homogenizer.

Details of dark field illumination module 260 are now explained with reference to FIG. 7.

Illumination units 265a, 265b, etc. are located around ring 261 and illuminate article 140. It is noted that an illumination unit can be a LED or may include a LED and one or more optical components such as lenses, mirrors and the like.

A hole 262 may be configured to collect part of the reflected\ scattered light from article 140 to imaging optics 120. It is noted that:

a. Any of the illumination units 265k, 265a, etc. may include a group of one or more LEDs and may include optics such as lenses;

b. The illumination units may densely cover all the periphery of the ring or only part of it.

c. All illumination units need not be identical—i.e. part of them may have different colors or shape to enable different modes of dark field illumination.

d. The illumination units may be activated at different times. As explained above, controller 210, pulse generator 220, and strip cables 230 provide for operation of different LEDs of different illumination units (or of the same illumination units) with different parameters (i.e. timing, pulse shape, pulse duration, pulse rate, pulse current, etc.). This enables the use of different modes of imaging during a single article scan—i.e. using different angle of illumination, different colors, etc.

Figure 7:
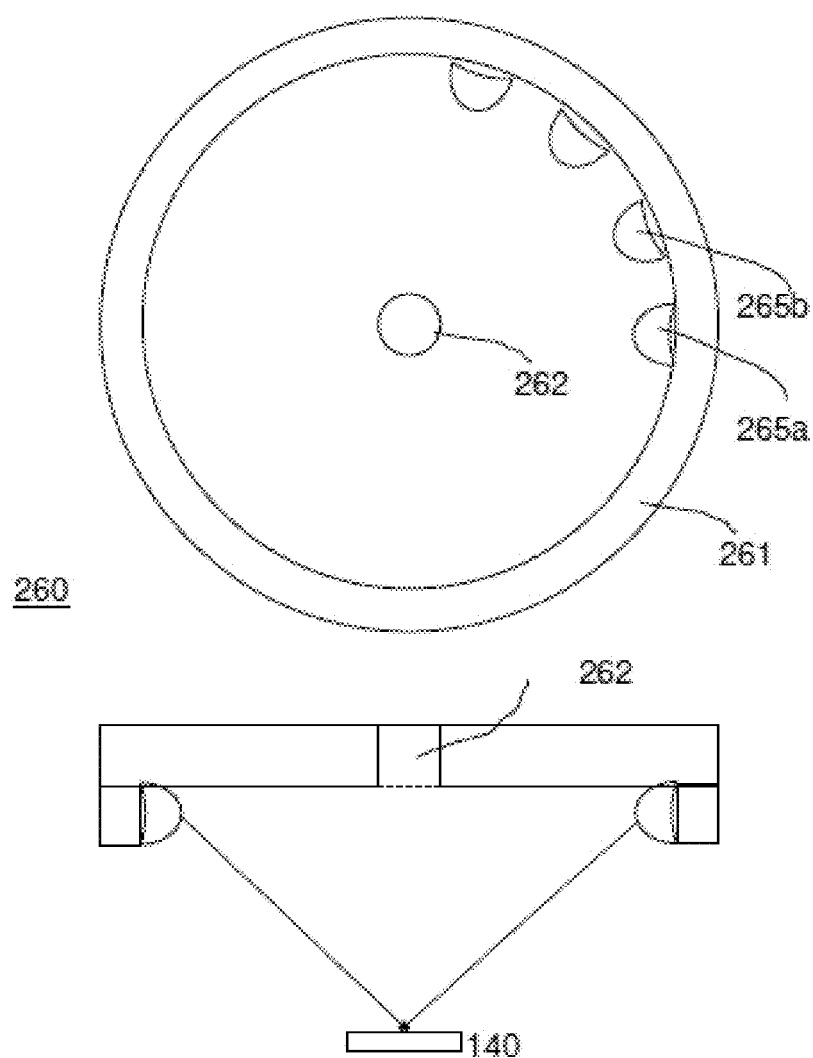
Figure 8:
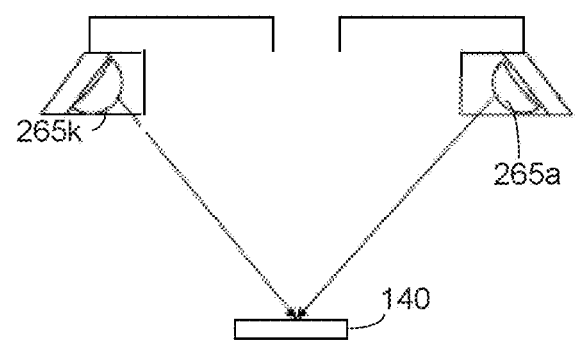
Figure 9:
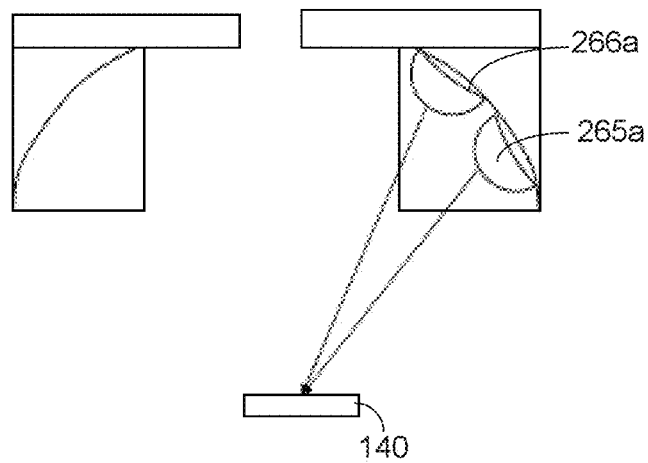
Figure 10:
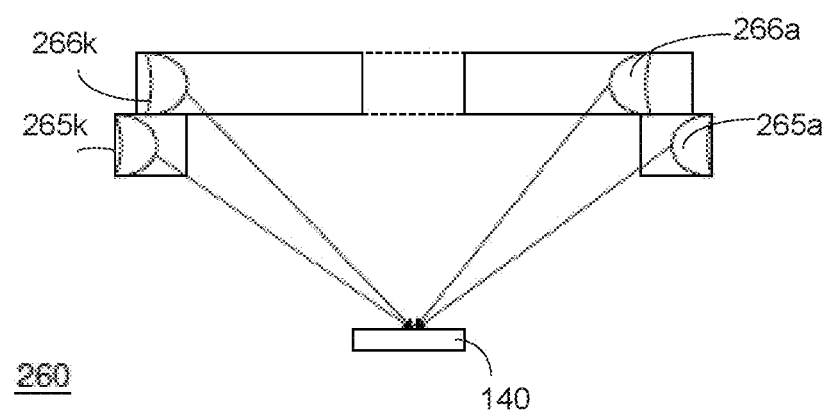

Illumination units 265a, 265b, 265k, 266a, 266k, 267a and 267k of FIGS. 7-10 and 15-18 are represented by half-circles—for simplicity of explanation. The optics included in each illumination unit can deflect the light pulses from one or more LEDs toward a desired direction. A desired direction can coincide (or be parallel to) with an optical axis of one or more LEDs of the illumination unit but may deviate from that optical axis. The former is illustrated in FIGS. 8 and 9 while the latter is illustrated in FIGS. 7 and 10.

The illumination units can be positioned in an annular formation—around (or within) one or more rings.

When the illumination units are arranged in multiple rings—the rings may be concentric, may be positioned at different heights or both.

Illumination units can be mounted in a vertical manner or in other oriented manner. Different illumination units of different rings can be oriented at different angles. When in vertical configuration a backplane of the illumination unit (that may support one or more LEDs) may be vertical—that is the illumination unit is aiming in a direction, which is parallel or near parallel to FOV (Field Of View) plan. The optical axis of the illumination unit is not necessarily coincides with the aiming direction of the illumination unit.

FIG. 7 provides a top view and a cross sectional view (along a vertical plane) of a single ring of vertically positioned illumination units 265a-265b and 265k that are connected to a ring 261. The ring 261 includes means of transferring high current pulses through the illumination units that are connected in series. Such means may be for example a flex PCB. At the center of the ring 261 there may be an aperture 262 for allowing bright field illumination on an article as well as collection of backscattered or reflected light from the article towards the imaging path.

FIG. 8 provides a cross sectional view (along a vertical plane) of a single ring of direct line-of sight oriented illumination units 265a and 265k that are connected to a ring 261. The illumination units may be oriented such that their optical axis may be directed towards the article and they are aiming at the center of FOV.

Figure 12:
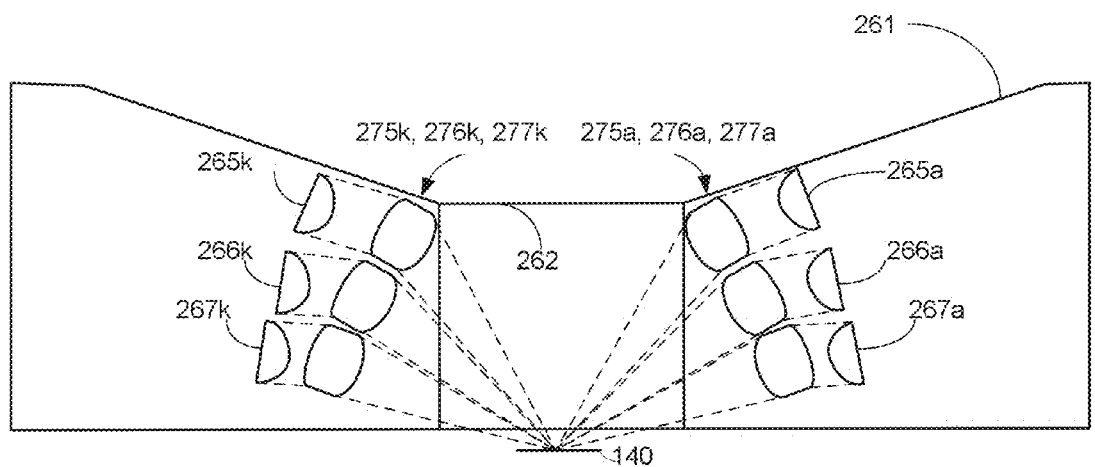
Figure 12A:
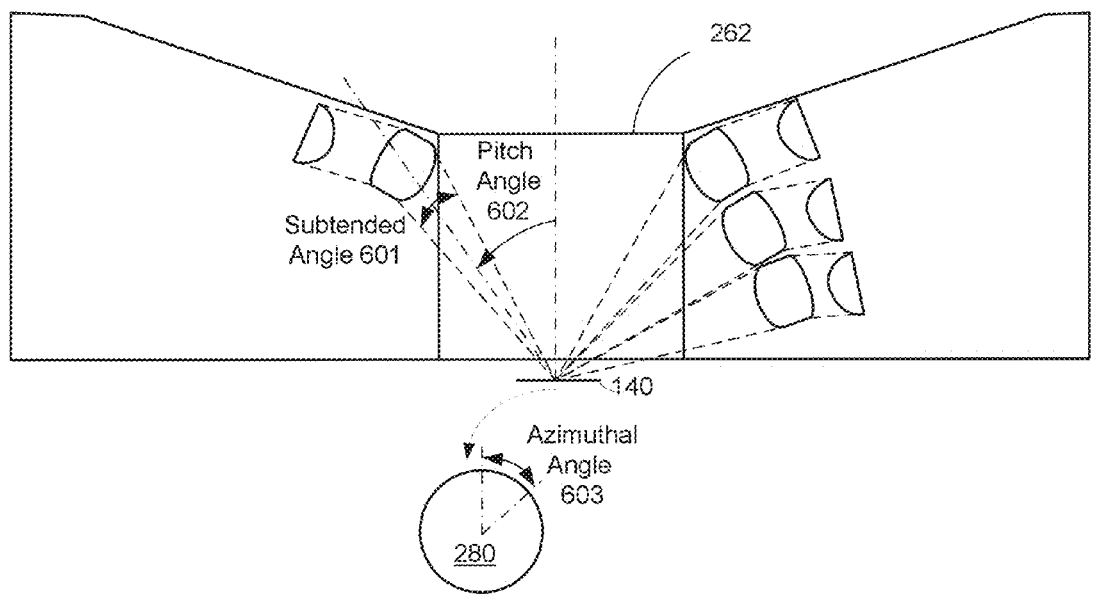

FIG. 9 provides a cross sectional view (along a vertical plane) of a two rings of direct line-of sight oriented illumination units 265a and 266a. One ring may be of smaller diameter than the other and may be positioned above the other ring to form a half-dome (or a partial half dome) configuration. The illumination units of the upper ring are in smaller pitch angle compare to the lower ring. Both optical axes of the illumination units are directed towards the article and they are aiming at the center of FOV. FIG. 12a illustrates a definition of a subtended angle 601, a pitch angle 602 and an azimuth angle 603. This provides for enhanced illumination intensity at the FOV and larger angular coverage range, or the ability to select between low and high illumination angles (pitch angle).

FIG. 10 provides a cross sectional view (along a vertical plane) of two rings of vertical illumination units 265a, 265k, 266a and 266k are stacked together for enhanced illumination intensity at the FOV and larger angular coverage range. One ring may be of smaller diameter than the other and may be positioned above the other ring to form a half-dome (or a partial half dome) configuration.

The illumination modules of FIGS. 9 and 10 may enable the use of different modes of operations, where in each mode only LEDs belong to either larger pitch angles or smaller pitch angles are operated.

Figure 15:
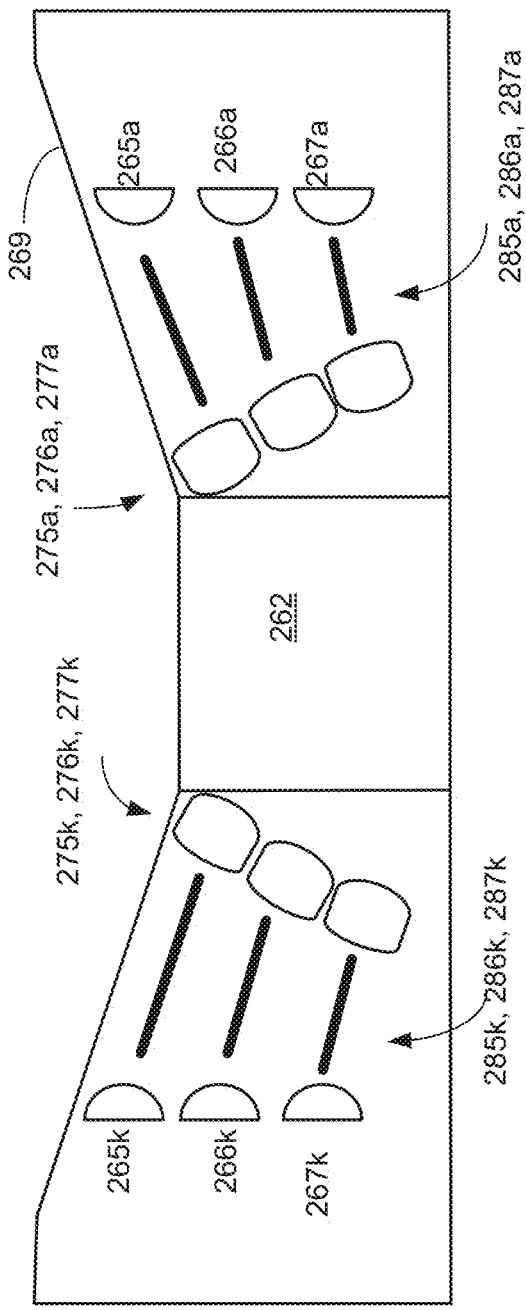

FIG. 15 shows an illumination module, which makes use of a lens array in front of an illumination unit along with light guides. The exit aperture of each light guide lies in the focal point of each lens. Each light guide may accept light emitted from a group of LEDs belonging to each illumination unit. Each LED of an illumination unit associated with a light guide focuses its light into its associated light guide. The light from each LED or an illumination unit (which may include several LEDs) is thus guided through the light guide and then focused\ imaged by associated lens onto the article FOV.

Lens 275a may be positioned in front of illumination unit 265a. Lens 275k may be positioned in front of illumination unit 265k. Lens 276a may be positioned in front of illumination unit 266a. Lens 276k may be positioned in front of illumination unit 266k. Lens 277a may be positioned in front of illumination unit 267a. Lens 277k may be positioned in front of illumination unit 267k. There may be additional levels of illumination units and lenses in various shapes and sizes to fill as required the entire hemispherical space above the article. Each of these lenses receives a light pulse from an illumination unit and focuses it onto the article (or another optical component positioned between the lens and the article) to a desired illumination area size. The illuminated area over the article may be of a circular, rectangular or any other desired shape and size depending on optical lens system design and requirements.

It is noted that the illumination module illuminates the inspected object by a circular area where light flux is decreasing from center of Field Of View (FOV) outwards (depending on the design).

It is noted that such lenses (275a, 276a, 277a, 275k, 276k and 277k) can follow (or be included in) each of the illumination units of other figures.

Figure 13:
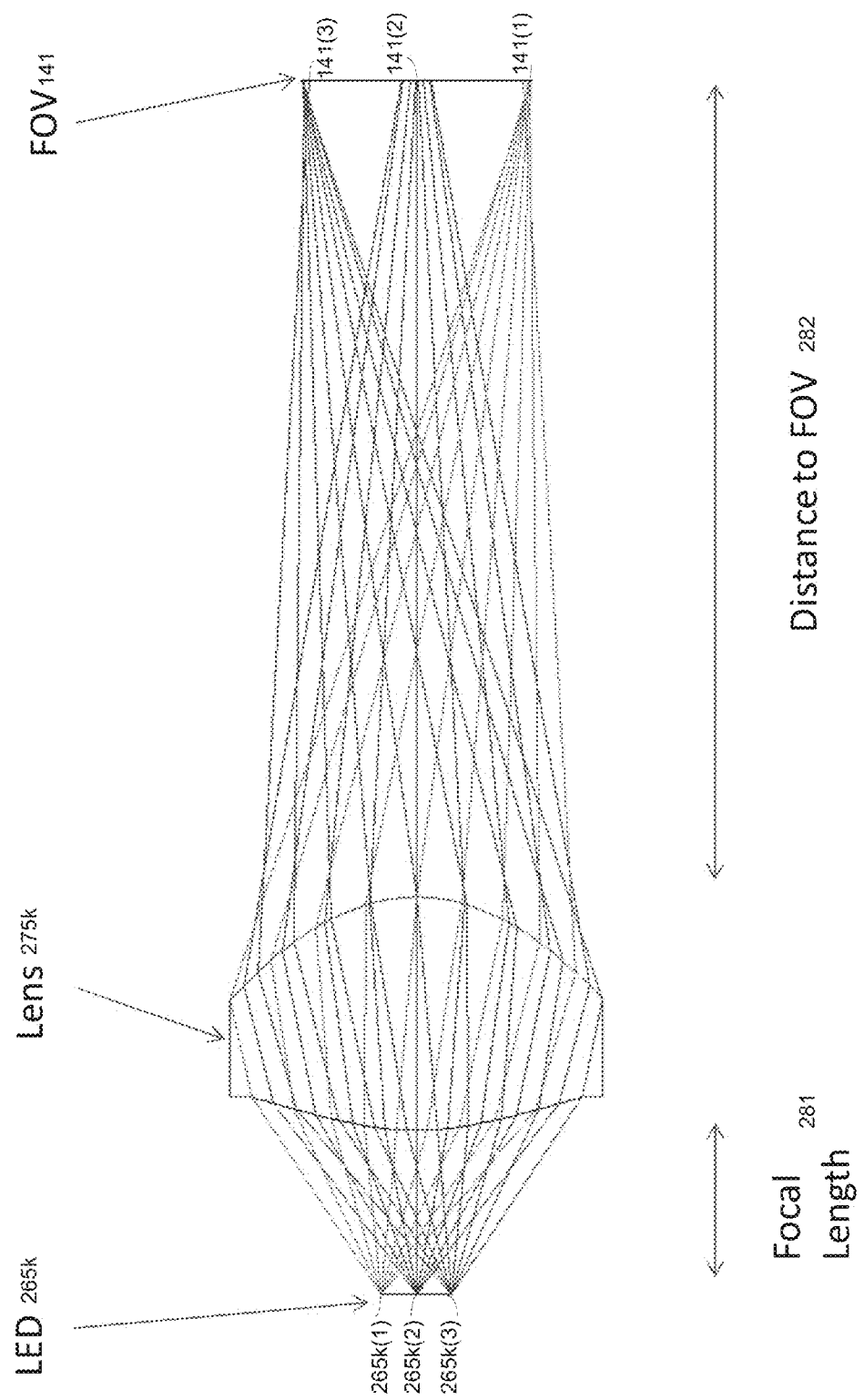
Figure 14:
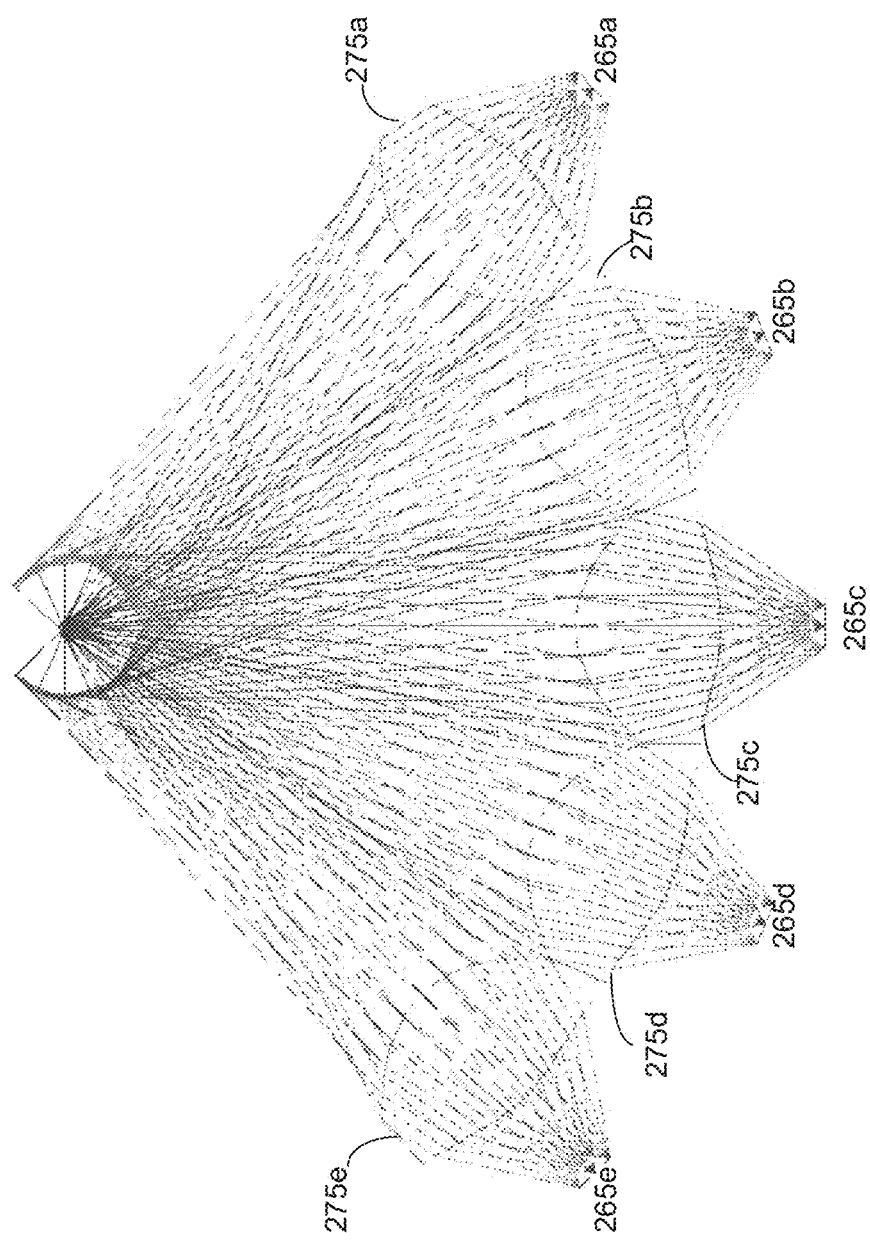

Each of these lenses may focus the light from each illumination unit over the entire required FOV—as illustrated in FIGS. 13 and 14.

Referring to FIG. 13—three groups of rays emanating from a single LED die 256k designated as red, green and blue i.e. 265k(3), 265k(1) and 265k(2) respectively, were arbitrarily selected (the Green and Red rays emanating from LED die rim while the Blue rays emanating from LED die center). Lens 275k focuses the light rays from the LED onto a field of view 141. The required FOV size is determined by LED die size, lens characteristics and distances from LED to lens and lens to FOV. As could be seen using infinite number of groups of rays emanating from LED die the rays after focusing by the lens will fill the entire FOV.

FIG. 13 illustrates the focal length 281 of the lens 275k and the distance 282 between the FOV 141 and the lens 275k.

The configuration of FIG. 14 may achieve high irradiance over the FOV 141 due to contributions from all the LEDs in a ring to the same FOV. In addition, it provides good light intensity uniformity over the entire FOV 141 azimuthally in the circular direction. For angle designation refer to FIG. 12a.

The pitch angle of a ring depends on the LED and on its associated lens characteristics and their locations with respect to FOV center. At each arbitrary point in the FOV, assuming it is small enough compare to the distance to illumination source, nearly the same Intensity (W/Sr) within the same angle coverage may be maintained. Larger angle coverage may be achieved by using additional LED rings as in FIGS. 9 and 10.

Referring back to FIG. 13—lens 275k can be positioned in front of the LED and may be shaped and positioned to preserve the brightness of the light pulses.

The annular positioning of the illumination units in a ring fashion may provide a uniform light patch at the FOV covering a certain angular range of illumination, designated angular coverage, in proportion with the subtended angle of the FOV center by the ring. Several such illumination rings each designed at different pitch angle may consequently produce several light patches at the FOV each covering a different range of illumination angles and when combining all together they will provide a larger angular coverage range. Different illumination angle ranges (i.e. different angle coverage) may be achieved by toggling different rings ON as desired for different applications inspection.

FIG. 14 illustrates a portion of a ring of illumination units' 265a-265e. Each LED of an illumination unit may be followed by a lens—such as lenses 275a-275e. Each LED is located at the focal plane of its associated lens. All lenses direct light pulses onto the article. As explained in relation to FIG. 13, the light from each LED fills the entire Field Of View. According to FIG. 14 the FOV at the article will be filled with light flux coming from different directions azimuthally, where there exists an illumination source of light and thus light will come from 360 degrees of a ring, which is entirely filled by illumination sources. Thus for example, a point at the center of FOV that is gazing at the illumination ring with the same pitch angle and with the same subtended angle "sees" nearly the same amount of light coming from different directions azimuthally. The resultant light image at the FOV due to illumination ring, which is fully filled with illumination sources, is thus a patch of light having a uniform irradiance at each point of the FOV and a uniform intensity (W/Sr) from all directions when gazing at the ring from FOV center.

Figure 11:
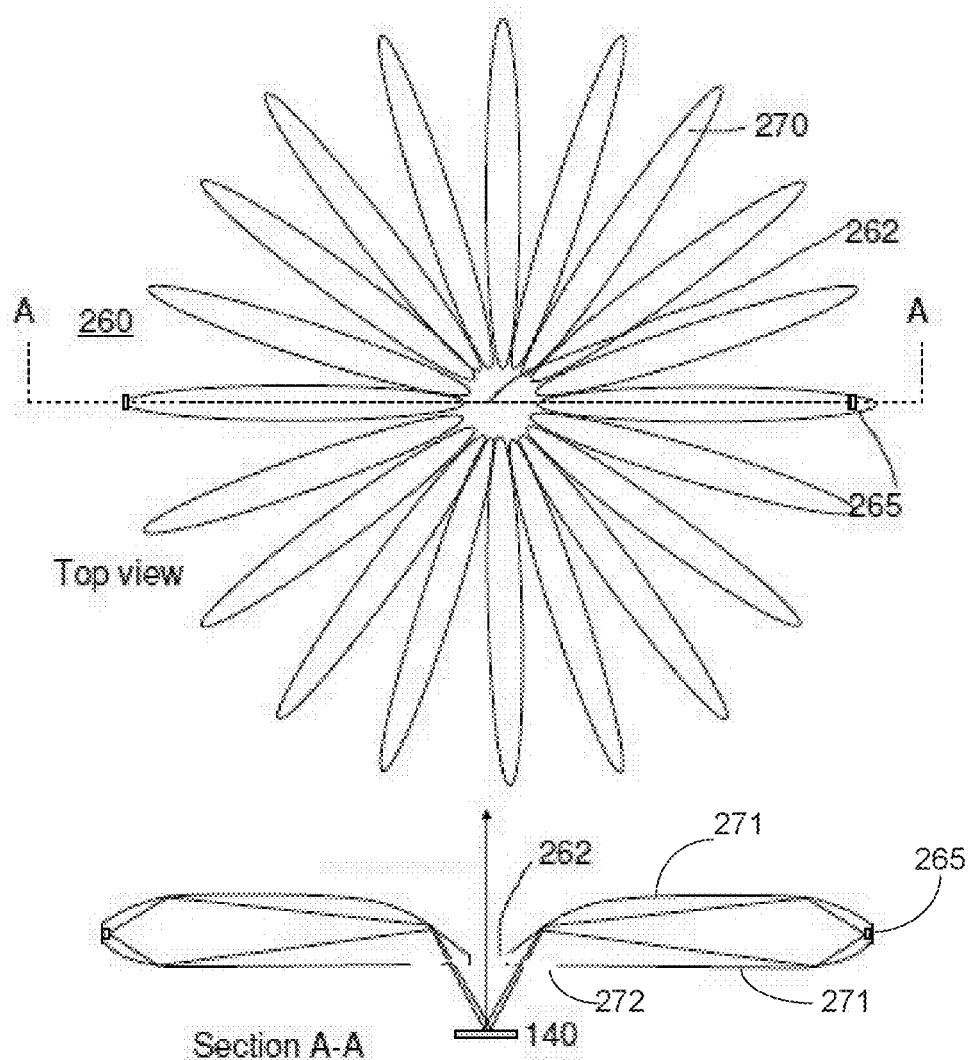

FIG. 11 shows an embodiment which illustrates the optical role of the ring using reflecting mirrors rather than lenses. A group of concentrators 270 are arranged around a hole 262 and configured to efficiently collect the light from LEDs 265 integrated into the concentrator and focuses it on a desired field of view on article 140. The concentrator may be a parabolic concentrator or other curved shape concentrator made of bulky solid material with high refractive index such as plastic like PMMA or other high index of refraction material. The concentrator boundaries reflect the light due to total internal reflection from the device boundaries and due to a reflective coating, which may or may not present on the outer surface of the concentrator.

In FIG. 11 the concentrators are illustrated as hollowed elliptical concentrators that include reflecting portions 271 for collecting and concentrating light emitted from associated LEDs and a transparent portion 272 through which light pulses propagate to the article. This configuration may use optimized angles of illumination for each sample.

As explained above, not all LEDs should be activated in a single high current short duration pulse. For example, LEDs of different rings can be activated at different points of time. Yet for another example—LEDs of the same ring but of different illumination units can activated at different times.

The selection of which LEDs to activate simultaneously can be based on at least one of the following: (i) Pitch and azimuth angle, (ii) height, (iii) illumination mode and (iv) color.

Figure 16:
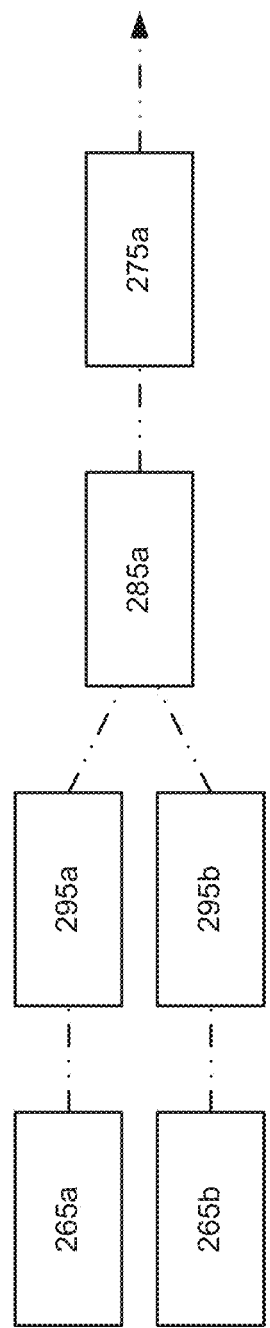

It is noted that different modes (angular, height, color) during the same scan, i.e. acquiring two images of each scanned area where one image may be acquired using low pitch angle illumination and another image of overlapping area may be acquired using a high pitch angle illumination FIGS. 15 and 16 illustrate a portion of an illumination module according to an embodiment of the invention.

According to this embodiment the LEDs of multiple illumination units are arranged in sets. The spectrum of light pulses of different LEDs of each set of LEDs differs from each other. Light pulses from LEDs of the same set of LEDs are directed towards a single light guide. Thus, light from LEDs 265a and 265b are directed, via coupling optics 295a and 295b onto light guide 285a that "mixes" these light pulses and outputs light pulses that have a spectrum that may be a superposition of the spectrums of light pulses from the LEDs of the set of LEDs. The light guide 285a may be followed by focusing optics 275a that focuses the light pulses onto the article. Thus—this embodiment virtually mixes two spectral ranges using a light guide and focuses the resultant mixed spectra over a FOV and may utilize all the advantages of previous embodiments.

An optimal light guide mixer may be a hexagonal Kaleidoscope, which mixes and homogenizes the light at the light guide output. The degree of homogenization depends on the light characteristics of the light source and Kaleidoscope characteristics. Basically a larger kaleidoscope length may be required for a narrower light cone of the light source in proportion to the inverse of the tangent of light cone angle.

This embodiment may require more space to apply in practice than previous embodiment. However, the advantage contained within this embodiment may be using the same optic system and gaining additional advantage—i.e. controlling the required light spectra at the FOV and achieving the full angular coverage for each color as in previous embodiment.

While FIG. 16 illustrates a pair of LEDs that are followed by coupling optics that are followed by a light guide and focusing optics, FIG. 16 being a cross sectional view illustrates only a single LED, a single coupling optics, the light guide and the focusing optics. Assuming that the LEDs are arranged in a ring formation, the other LED and coupling optics are placed along the ring such as to extend from the page of FIG. 15.

Each light source may be coupled using a proper optics into a light guide entrance aperture. The light guide mixes and homogenizes the two spectra at its output aperture. The mixed light spectrum may be then focused at the FOV to create a mixed spectra intensity image (i.e. a patch of light), which may be controlled to choose either a separate color image or a mixed color image.

The light source in this embodiment may include also RGB or RGBY or any mix of dies type of a LED. The coupling optics to light guide in this case may not be necessary.

Figure 17:
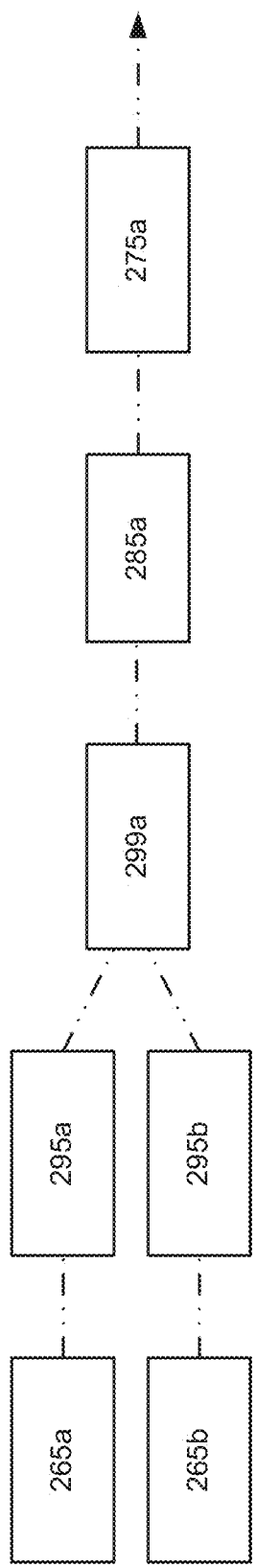

FIG. 17 illustrates a portion of the illumination module that further includes a dichroic (interference) filter 299a that may be located between the coupling optics 295a and 295b and light guide 285a. This dichroic filter 299a can preserve the brightness of each color spectrum and still maintain the other features of controlling the colors and achieving a full angular coverage for each color.

Figure 18:
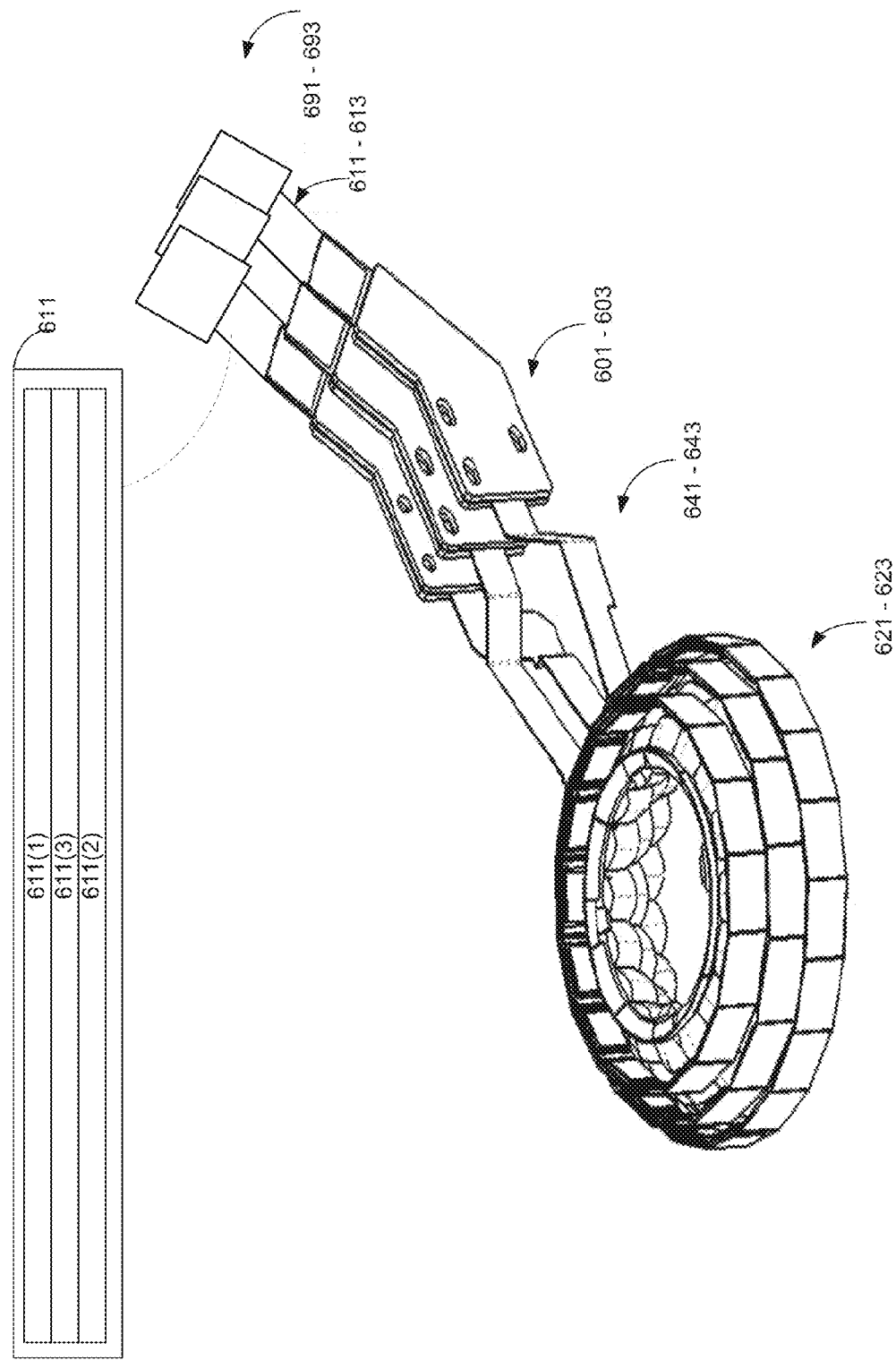

FIG. 18 illustrates, for example, three rings of illumination units 621-623, PCB base elements 641-643, strip cables 611-613, intermediate connectors 601-603 and LED drivers 691-

693. The intermediate connectors 601-603 are connected between PCB base elements 641-643 and the strip cables 611-613. The LEDs in each ring are connected to the PCB base elements 641-643 that provide structural supports and electrical connectivity such that the LEDS of the illumination units 621-623 may be connected in various manners such as but not limited to a serial manner. The PCB base elements, once providing serial connectivity. Units 611-613 are formed using a Kapton and adhesive tapes much like a strip line cable concept. FIG. 18 also illustrates an out of scale cross section of strip cable 611—it includes two thin and long conductors 611(1) and 611(2) as well as a thin and long isolating Kapton material 611(3) along with adhesive tape which are sandwiched together in between 611(1) and 611(2).

FIGS. 21-25 illustrate various portion of the system according to various embodiments of the invention.

Figure 21:
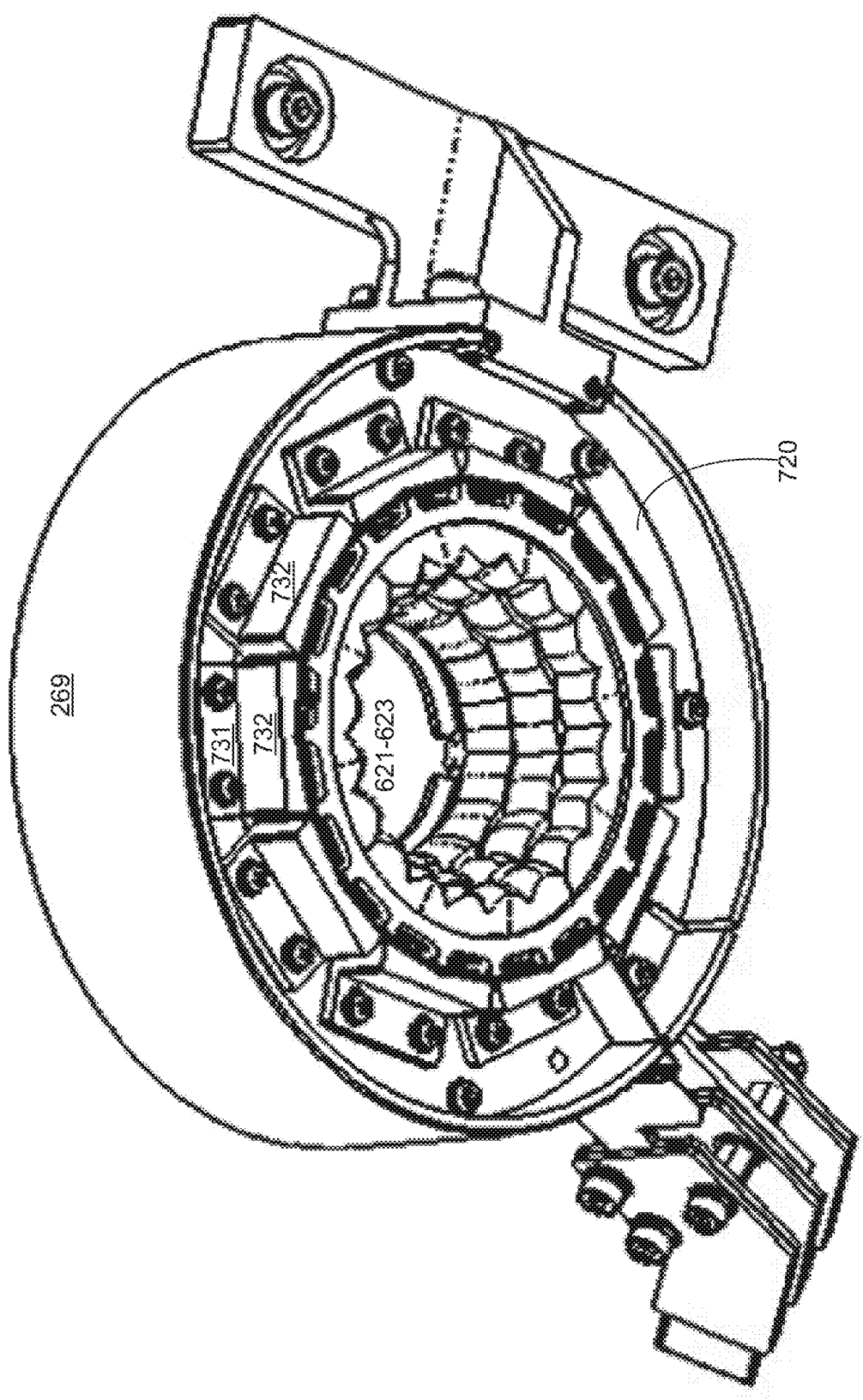
FIGS. 21-25 illustrate various portion of the system according to various embodiments of the invention.
Figure 22:
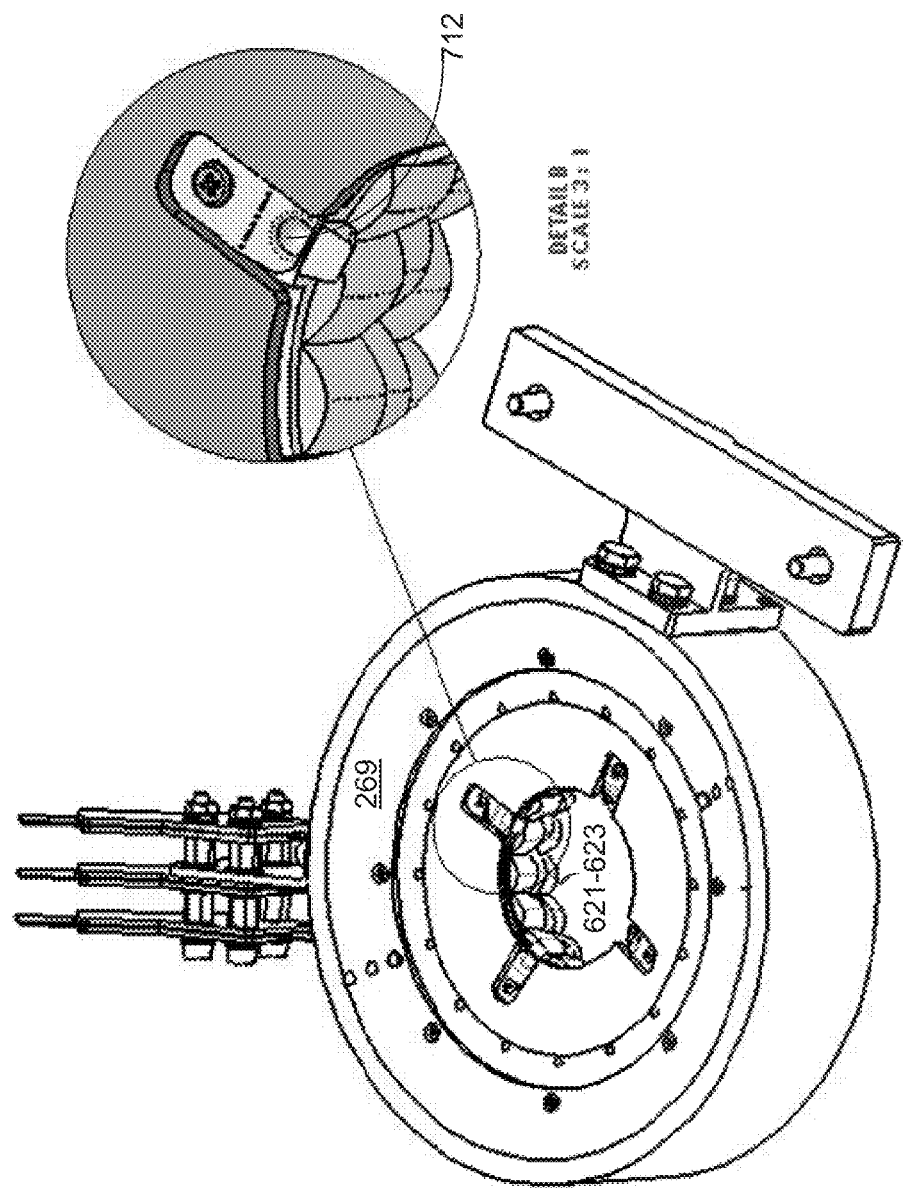
Figure 23:
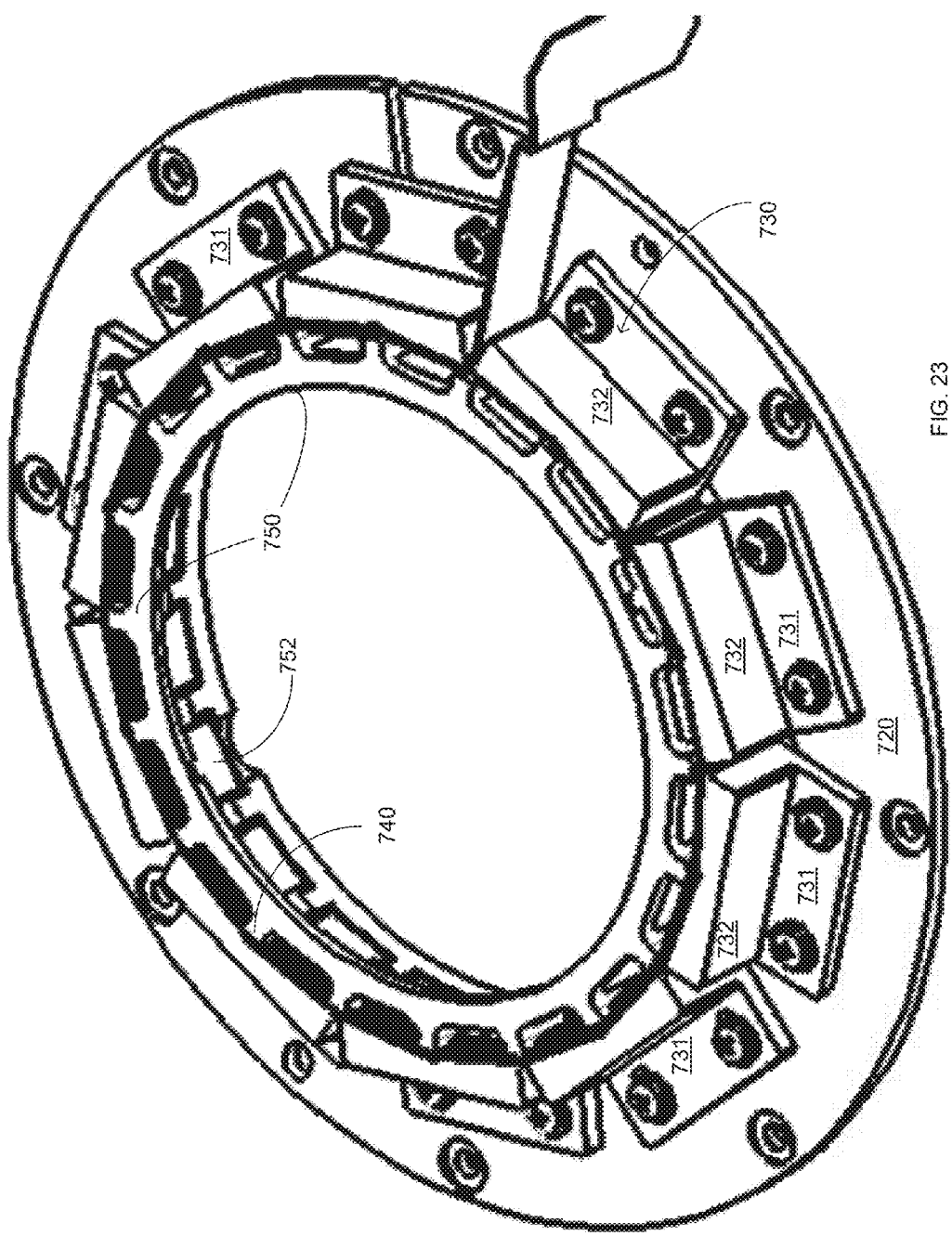
Figure 24:
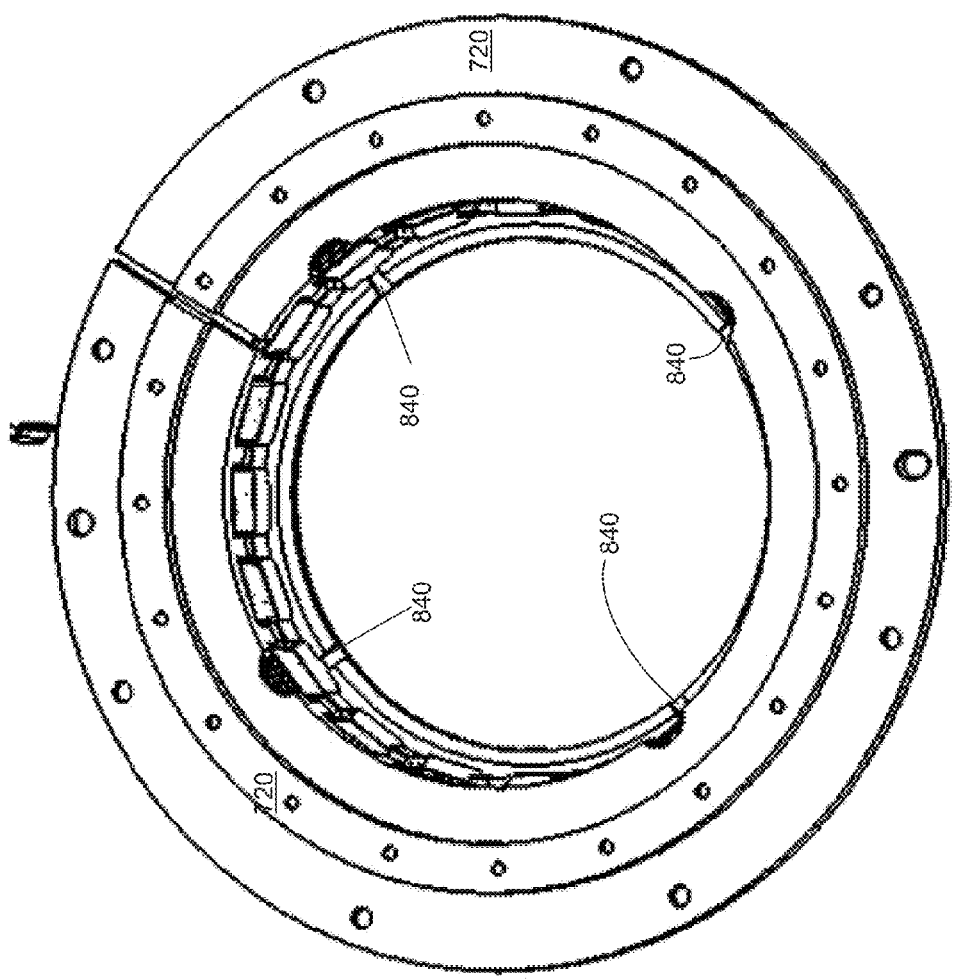
Figure 25:
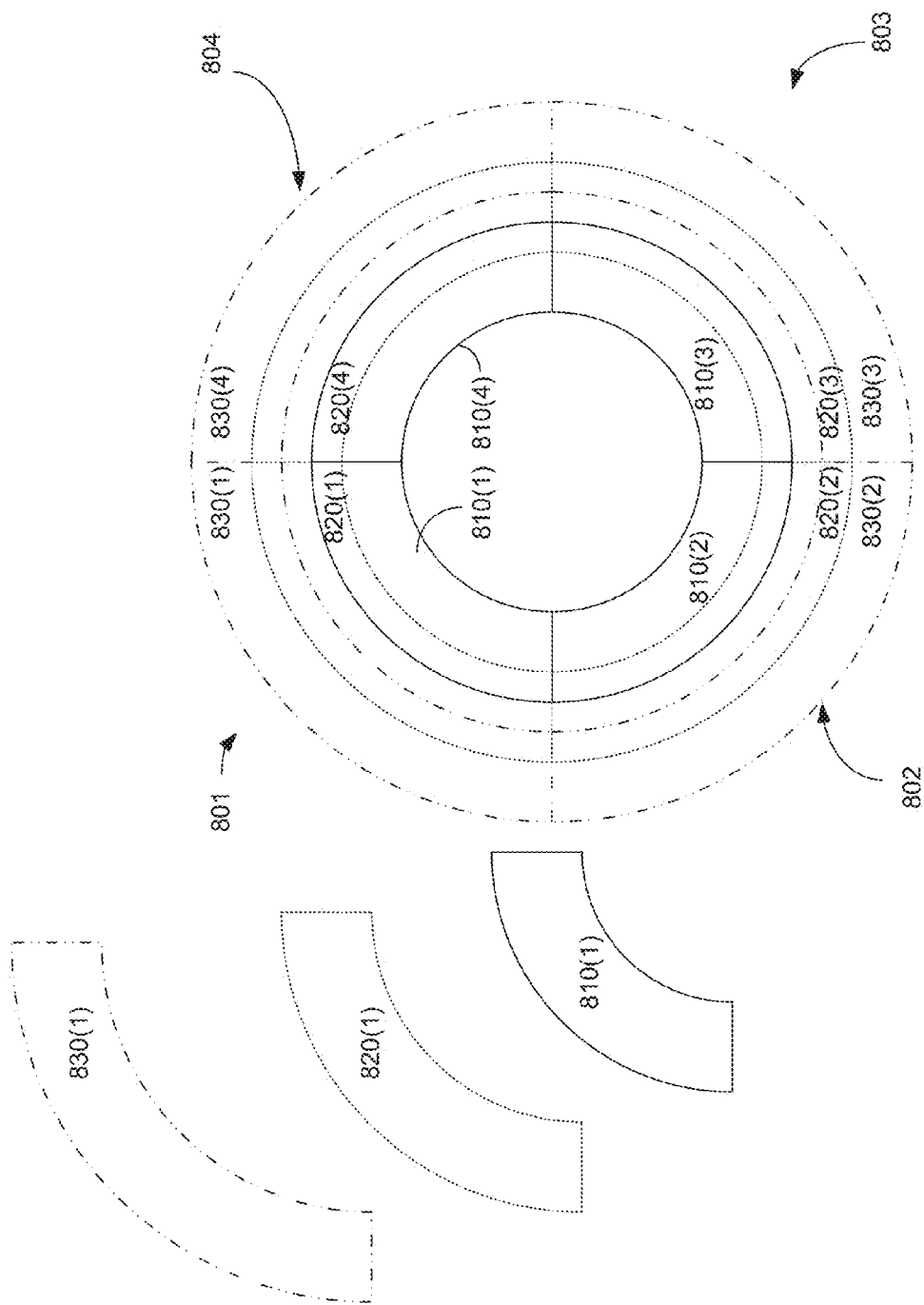

FIG. 21 is a bottom view of annular supporting element 269 and three illumination units 621-623 according to an embodiment of the invention. FIG. 22 is a top view of annular supporting element 269, three illumination units 621-623 and of a spring element 712 according to an embodiment of the invention. FIG. 23 is a top view of a portion of a first illumination unit 621 according to an embodiment of the invention. FIG. 24 is a bottom view of a portion of a first illumination unit 621 according to an embodiment of the invention. FIG. 25 is a schematic view of lens array segments 810(1)-830(4) according to an embodiment of the invention.

The system includes three concentric illumination units 621-623 that may differ by size and (once assembled) by height of assembly. Each illumination unit includes multiple lenses. The first illumination unit 621 is positioned on top of the second illumination unit 622 while the lowest illumination unit is the third illumination unit 623.

Referring to FIG. 23, each illumination unit may include:
a. An annular (horizontal) base 720.
b. Multiple connectors such as:
  i. External connectors 730, each including a horizontal portion 731 that is connected to the annular base and a vertical portion 732.
  ii. Inner connectors 750.
c. A LED base element 740 that can be flexible, made of flexible materials or made of fragments of a PCB that are connected to each other so as to enable a movement between different fragments. LEDs are connected to the LED base element 740.

It is noted that either one of the connectors can be integrated with the annular base 720 is can be, for example, shaped as a cylinder that is perpendicular to the annular base and have windows formed within. The LEDs can be placed to face windows (such as window 752) that are formed by the inner connectors 750.

According to an embodiment of the invention the lens array can act as an inner connector—a mold of each lens of the lens array can include a space in which a LED can be inserted.

The LED base element 740 is connected to one or more connectors. FIGS. 21-24 illustrate the LED base element 740 as being placed (once assembled) between the vertical portion 732 of the external connectors 730 and a vertical portion of the inner connectors 750. These connectors (730, 750) can be fastened against each other after the insertion of the LED base element 740. The fastening can be made by various fastening elements such as screws and the like.

The number of connectors and their shape may differ from those illustrated in FIGS. 21-24.

LEDS are connected to the LED base element and may provide serial connectivity. FIG. 23 illustrates the LED base element 740 as being connected to strip lines that extend out of the external connectors 730. It is noted that either one of the internal and external connectors can include multiple separate portions—that can be connected to the annular base one after the other.

The annular bases of the different illumination units can be connected to each other—preferably after connecting the LED base element to each illumination unit. Three annular arrays of lenses 265, 266 and 267 can be connected to one or more of the annular bases—either directly of via additional connecting elements.

According to an embodiment of the invention each array of lenses is separated to four segments—that are separated from each other along imaginary vertical axes—each covering an angular range of about ninety degrees. The illumination segments of different illumination units that correspond to the same angular range can be connected to each other. Referring to FIG. 25—each lens array of each illumination unit (261, 262 and 263) is split to four portions and corresponding portions of different lens arrays may be connected together. Accordingly—the lens array of the first illumination unit 261 is segmented to four segments 810(1), 810(2), 810(3) and 810(4). The lens array of the second illumination unit 262 is segmented to four segments 820(1), 820(2), 820(3) and 820(4). The lens array of the third illumination unit 263 is segmented to four segments 830(1), 830(2), 830(3) and 830(4). FIG. 25 illustrates the different lens arrays as being partially overlapping. When connected to each other corresponding lens array portions can be connected to each other—thus segments 810(1), 820(1) and 830(1) are connected to each other. Segments 810(2), 820(2) and 830(2) are connected to each other. Segments 810(3), 820(3) and 830(3) are connected to each other. Segments 810(4), 820(4) and 830(4) are connected to each other.

Each group of segments can be connected to the annular ring 720 of the third illumination unit 263. Each group of segments can include a pin that matches a notch formed at the annular ring 270 such as to prevent the group of segments to rotate or otherwise move in relation to the LEDs of the illumination units 261-263. These notches are denoted 840 in FIG. 24. The different groups of segments are also forced against each other (thus preventing unnecessary movement) by spring element—as shown in FIG. 22—in which one spring element is forces against each one of segments 810(1)-810(4).

It is noted that the illumination units can be connected—one illumination unit after the other—starting by the annular ring, LED base and other structural elements and finally fastening the segments of the lens arrays to these elements.

The mentioned configuration illustrated in FIGS. 21-25 can be highly accurate—and thus improves the optical performance of the illumination units. Additionally or alternatively, most components (such as an annular base 720, external supporting elements 730 and inner structural element 750) can be made of heat conducting materials (such as metal) that can assist in dissipating the heat generated by the LEDs once activated.

The lenses (lens array fragments) are integrated into the mechanical elements (720, 730) and this arrangement is also very compact.

It is noted that the lens array of each ring can be separated from lens arrays of other rings.

Figure 19:
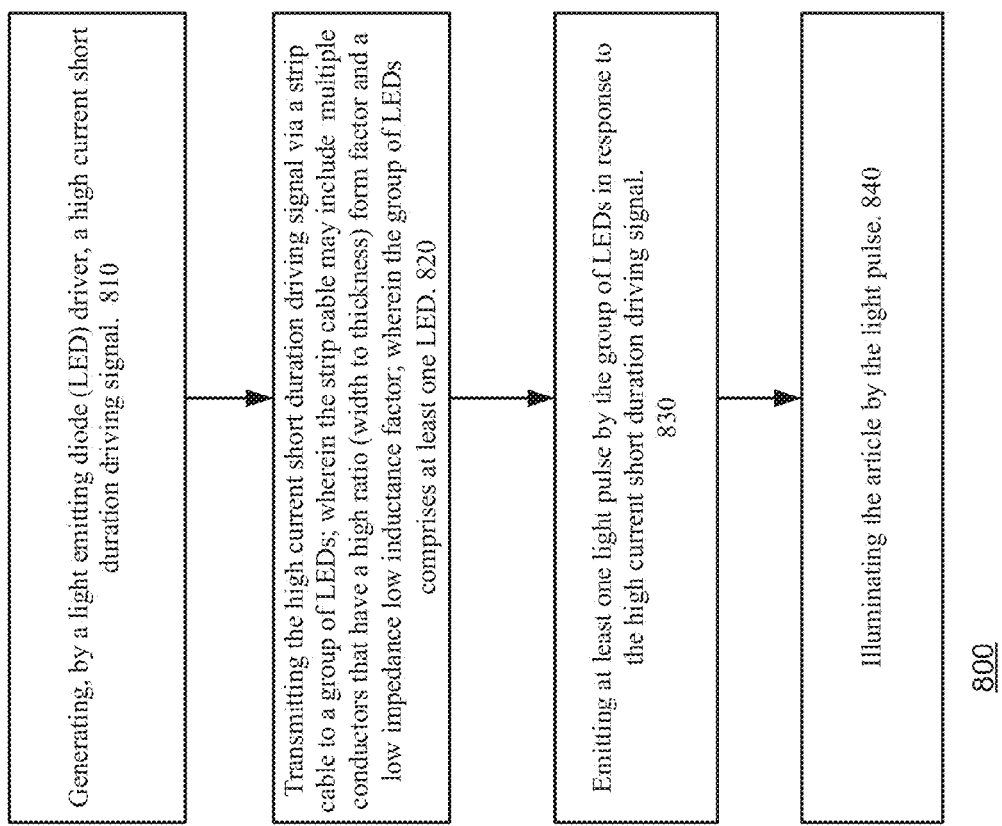
FIGS. 19-20 illustrate methods according to various embodiments of the invention.
Figure 20:
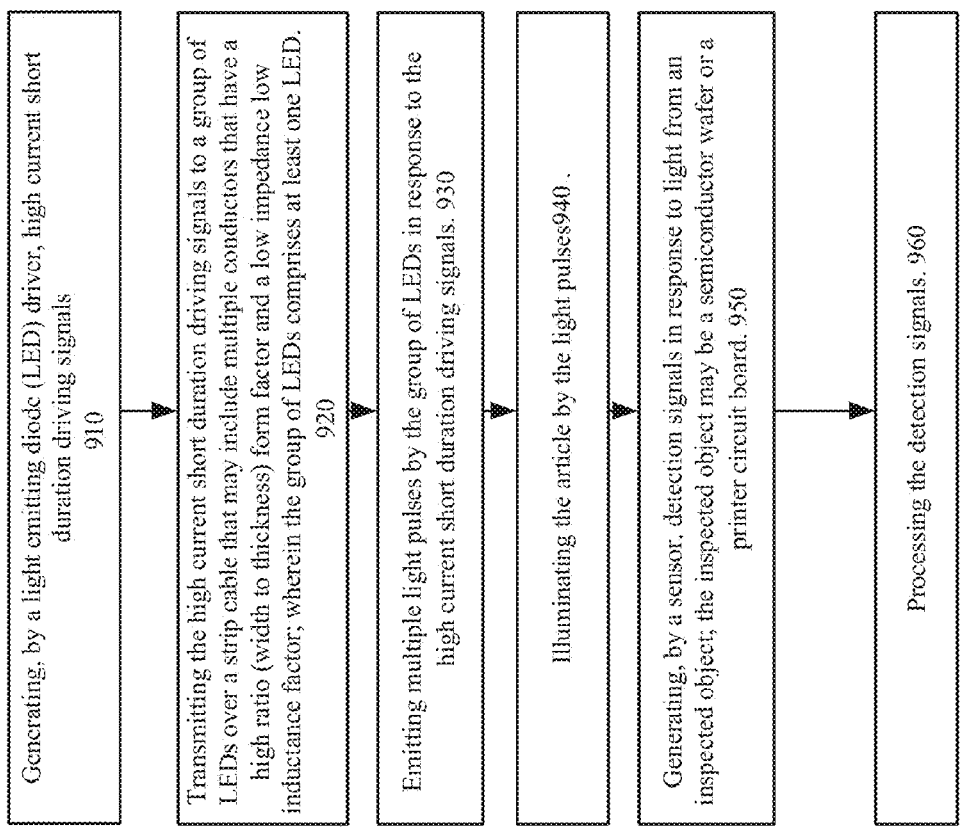

FIGS. 19 and 20 illustrate methods 800 and 900 according to various embodiments of the invention.

FIG. 19 illustrates method 800 according to an embodiment of the invention. Method 800 can be executed by any of the mentioned above illumination modules or systems.

Method 800 starts by stage 810 of generating, by a light emitting diode (LED) driver, a high current short duration driving signal.

Stage 810 may be followed by stage 820 of transmitting the high current short duration driving signal via a strip cable to a group of LEDs; wherein the strip cable may include multiple conductors that have a high form factor and a low impedance low inductance factor; wherein the group of LEDs comprises at least one LED.

Stage 820 may be followed by stage 830 of emitting at least one light pulse by the group of LEDs in response to the high current short duration driving signal.

Stage 830 may be followed by stage 840 of illuminating the article by the light pulse.

Stages 810-840 can be repeated multiple times, for illuminating one or more areas of the article. A movement can be introduced between iterations of stage 810-840.

FIG. 20 illustrates method 900 for inspecting an article, according to an embodiment of the invention.

Method 900 can start by stage 910 of generating, by a light emitting diode (LED) driver, high current short duration driving signals.

Stage 910 may be followed by stage 920 of transmitting the high current short duration driving signals to a group of LEDs via a strip cable that may include multiple conductors that have a high form factor, low impedance and a low inductance factor; wherein the group of LEDs includes at least one LED.

Stage 920 may be followed by stage 930 of emitting multiple light pulses by the group of LEDs in response to the high current short duration driving signals.

Stage 930 may be followed by stage 940 of illuminating the article by the light pulses.

Stage 940 may be followed by stage 950 of generating, by a sensor, detection signals in response to light from an inspected object; the inspected object may be a semiconductor wafer or a printer circuit board.

Stage 950 may be followed by stage 960 of processing the detection signals.

Stages 910-960 can be repeated multiple times, for illuminating one or more areas of the article. A movement can be introduced between iterations of stages 910-960.

Each one of method 800 and 900 can include:
a. Using a high current high short duration driving signal that has a current that can be below or exceed 100 Amperes.
b. Using a high current short duration driving signal that has a current that can exceed a maximal allowable current to be provided to the group of LEDs when operating in a continuous illumination mode.
c. Using a strip cable that has a high form factor that may range between 8 and 40.
d. Using a strip cable that has a high form factor that may exceed 30.
e. Generating light pulses by multiple groups of LEDs, each group of LEDs being fed by a strip cable.
f. Independently controlling each group of LEDs out of multiple groups of LEDs.
g. Using a group of LEDs that are arranged in a ring formation and wherein each LED may be followed by optics for directing light from the LED towards an article.
h. Emitting multiple light pulses by multiple groups of LEDs, wherein the multiple groups of LEDs that are arranged in a concentric rings formation and wherein each LED may be followed by optics for directing light from the LED towards an article.
i. Using a group of LEDs that includes multiple sets of LEDs; the spectrum of light pulses of different LEDs of each set of LEDs differs from each other.
j. Directing light pulses from LEDs of the same set of LEDs towards a single light guide; and outputting, by each light guide, light pulses that have a spectrum that may be a superposition of the spectrums of light pulses from the LEDs of the set of LEDs.
k. Emitting multiple light pulses by multiple groups of LEDs towards multiple hollow concentrators that are located in a first plane; receiving, by each hollow concentrator, the multiple light pulses; and directing, by each hollow concentrator, a light pulse from the group of LEDs towards an article that may be positioned outside the first plane.
l. Using groups of LEDs that are positioned at an annular formation; wherein the multiple hollow concentrators have a parabolic shape and radially extend from a center of the illumination module.
m. Emitting multiple light pulses by multiple groups of LEDs that are positioned in a half dome formation.
n. Illuminating, by the group of LEDs, a collimator with light pulses; collimating the multiple light pulses by the collimator to provide collimated light pulses; spectrally filtering, by a spectral filter, the collimated light pulses to provide filtered light pulses; increasing, by a homogenizer, an illumination homogeneity of the filtered light pulses to provide homogenized light pulses; and concentrating, by a concentrator, the homogenized light pulses onto a light guide.
o. Using a concentrator that is a compound parabolic concentrator; and wherein the filter belongs to a set of replaceable filter.

Either one of the methods can include:
a. Transmitting the high current short duration driving signal via the strip cable and a LED base element to a group of LEDs; and wherein the LED base element is coupled to at least a portion of the group of LEDs; wherein the LED based element is connected to at least one connector; wherein the at least one connector is coupled to an annular base; wherein the at least one connector and the annular base are made of heat conducting material; and dissipating heat generated by the at least portion of the LEDs by the at least one connector and the annular base.
b. Emitting multiple light pulses by multiple groups of LEDs in response to the high current short duration driving signals; wherein the multiple groups of LEDs are coupled to multiple LED base elements, multiple connectors and multiple annular bases; wherein different LED base elements are connected to multiple concentric annular bases.
c. Emitting multiple light pulses by multiple groups of LEDs in response to the high current short duration driving signals; wherein the multiple groups of LEDs are coupled to multiple LED base elements, multiple connectors and multiple annular bases; wherein the multiple annular bases are positioned at different heights and wherein at least one segment of a lens array is connected to each annular base.
d. Emitting multiple light pulses by multiple groups of LEDs in response to the high current short duration driving signals; wherein the multiple groups of LEDs are coupled to multiple LED base elements, multiple connectors and multiple annular bases, wherein the multiple annular bases are positioned at different heights and multiple segments of lens arrays are connected to a single annular base.

e. Directing the multiple light pulses via multiple lens array segments, wherein the multiple lens array segments are forced against each other, once assembles, by spring elements.

f. Directing the multiple light pulses via multiple lens array segments, wherein lens array segments differ from each other by at least one of a height of assembly and angular range.

The present invention can be practiced by employing conventional tools, methodology and components. Accordingly, the details of such tools, components and methodology are not set forth herein in detail. In the previous descriptions, numerous specific details are set forth, such as shapes of cross sections of typical lines, amount of deflection units, etc., in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. An inspection system comprising:
   a LED driver;
   a group of light emitting diodes (LEDs) that comprises at least one LED; the group of LED is coupled to the LED driver; wherein the LED driver is arranged to activate the group of LEDs by driving a high current short duration driving signal; and wherein the group of LEDs is arranged to emit at least one light pulse in response to the high current short duration driving signal;
   a collimator;
   a filter;
   a homogenizer; and
   a concentrator;
      wherein the group of LEDs is arranged to illuminate the collimator by light pulses;
      wherein the collimator collimates the light pulses to provide collimated light pulses;
      wherein the filter is arranged to spectrally filter the collimated light pulses to provide filtered light pulses;
      wherein the homogenizer is arranged to increase an illumination homogeneity of the filtered light pulses to provide homogenized light pulses; and
      wherein the concentrator is arranged to concentrate the homogenized light pulses onto a light guide.

2. The inspection system according to claim 1, wherein the high current short duration driving signal has a current that exceeds 100 Amperes.

3. The inspection system according to claim 1, wherein the high form factor exceeds 30.

4. The inspection system according to claim 1, comprising multiple groups of LEDs.

5. The inspection system according to claim 1, comprising multiple groups of LEDs, each group of LEDs being controlled independently from other groups of LEDs.

6. The inspection system according to claim 1, wherein the group of LEDs is arranged in a ring formation and wherein each LED is followed by optics for directing light from the LED towards an article.

7. The inspection system according to claim 1, comprising multiple groups of LEDs that are arranged in a concentric rings formation and wherein each LED is followed by optics for directing light from the LED towards an article.

8. The inspection system according to claim 1, wherein the group of LEDs comprises multiple sets of LEDs;
   wherein the spectrum of light pulses of different LEDs of each set of LEDs differs from each other;
   wherein light pulses from LEDs of the same set of LEDs are directed towards a single light guide;
   wherein each light guide is arrange to output light pulses that have a spectrum that is a superposition of the spectrums of light pulses from the LEDs of the set of LEDs.

9. The inspection system according to claim 1, comprising multiple groups of LEDs and multiple hollow concentrators that are located in a first plane;
   wherein each hollow concentrator is positioned to receive lights pulses from a group of LEDs, and direct the light from the group of LEDs towards an article that is positioned outside the first plane.

10. The inspection system according to claim 9, wherein the groups of LEDs are positioned at an annular formation; wherein the multiple hollow concentrators have a parabolic shape and radially extend from a center of the illumination module.

11. The inspection system according to claim 1, wherein the concentrator is a compound parabolic concentrator; and wherein the filter belongs to a set of replaceable filters.

12. The inspection system according to claim 1, further comprises:
   a LED base element that is coupled to at least a portion of the group of LEDs;
   at least one connector arranged to be connected to the LED base element;
   an annular base the is coupled to the at least one connector;
   wherein the at least one connector and the annular base are made of heat conducting material for dissipating heat generated by the at least portion of the LEDs.

13. The inspection system according to claim 12, comprising multiple LED base elements; multiple connectors and multiple annular bases; wherein a plurality of LEDS are connected to each LED base element; wherein different LED base elements are connected to multiple concentric annular bases.

14. The inspection system according to claim 13, wherein the multiple annular bases are positioned at different heights and wherein at least one segment of a lens array is connected to each annular base.

15. The inspection system according to claim 13, wherein the multiple annular bases are positioned at different heights and multiple segments of lens arrays are connected to a single annular base.

16. The inspection system according to claim 13, further comprising multiple segment of lens arrays that are forced against each other, once assembles, by spring elements.

17. The inspection system according to claim 13, comprising multiple lens array segment, wherein lens array segments differ from each other by at least one of a height of assembly and angular range.

18. The inspection system according to claim 1 further comprising:
- a sensor for generating detection signals in response to light from an inspected object; the inspected object is a semiconductor wafer or a printer circuit board; and
- a processor for processing the detection signals.

19. A method for inspecting an article, the method comprising:
- generating, by a light emitting diode (LED) driver, a high current short duration driving signal;
- transmitting the high current short duration driving signal to a group of LEDs; wherein the group of LEDs comprises at least one LED;
- emitting light pulses by the group of LEDs thereby illuminating a collimator in response to the high current short duration driving signal;
- collimating, by the collimator, the light pulses to provide collimated light pulses;
- spectrally filtering, by a filter, the collimated light pulses to provide filtered light pulses;
- increasing, by a homogenizer, an illumination homogeneity of the filtered light pulses to provide homogenized light pulses;
- concentrating, by a concentrator, the homogenized light pulses onto a light guide; and
- illuminating the article by the homogenized light pulses.

20. The method according to claim 19, wherein the high current high short duration driving signal has a current that exceeds 100 Amperes.

21. The method according to claim 19 further comprising:
- emitting multiple light pulses by the group of LEDs in response to the high current short duration driving signals;
- illuminating the article by the homogenized light pulses;
- generating, by a sensor, detection signals in response to light from an inspected object; the inspected object is a semiconductor wafer or a printer circuit board; and
- processing the detection signals.

* * * * *